US012781425B2

(12) United States Patent
Park et al.

(10) Patent No.: US 12,781,425 B2
(45) Date of Patent: Nov. 3, 2026

(54) CLOTHING TREATMENT APPARATUS AND METHOD FOR CONTROLLING CLOTHING TREATMENT APPARATUS

(71) Applicant: LG Electronics Inc., Seoul (KR)

(72) Inventors: Sunghoo Park, Seoul (KR); Minji Kim, Seoul (KR); Jaehyung Kim, Seoul (KR); Jinhyuk Jang, Seoul (KR); Yongji Park, Seoul (KR); Sunyong Kim, Seoul (KR); Eunji Shin, Seoul (KR); Hyosoo Kim, Seoul (KR)

(73) Assignee: LG Electronics Inc., Seoul (KR)

(*) Notice: Subject to any disclaimer, the term of this patent is extended or adjusted under 35 U.S.C. 154(b) by 170 days.

(21) Appl. No.: 18/833,760

(22) PCT Filed: Jan. 27, 2023

(86) PCT No.: PCT/KR2023/001260
§ 371 (c)(1),
(2) Date: Jul. 26, 2024

(87) PCT Pub. No.: WO2023/146338
PCT Pub. Date: Aug. 3, 2023

(65) Prior Publication Data

US 2025/0129541 A1 Apr. 24, 2025

(30) Foreign Application Priority Data

Jan. 28, 2022 (KR) ........................ 10-2022-0013011
Jan. 28, 2022 (KR) ........................ 10-2022-0013023
(Continued)

(51) Int. Cl.
*D06F 73/02* (2006.01)
*A61L 2/07* (2006.01)

(52) U.S. Cl.
CPC ................ *D06F 73/02* (2013.01); *A61L 2/07* (2013.01)

(58) Field of Classification Search
CPC .................................. D06F 73/02; A61L 2/07
(Continued)

(56) References Cited

U.S. PATENT DOCUMENTS

2011/0132043 A1 6/2011 Kim
2011/0138542 A1 6/2011 Ji et al.
(Continued)

FOREIGN PATENT DOCUMENTS

EP 3228742 A1 10/2017
EP 3252210 A1 12/2017
(Continued)

OTHER PUBLICATIONS

KR20110035030A—machine translation (Year: 2011).*
(Continued)

*Primary Examiner* — Tinsae B Ayalew
(74) *Attorney, Agent, or Firm* — Fish & Richardson P.C.

(57) ABSTRACT

The present invention relates to a clothing treatment apparatus, in which a steam generator for generating steam includes a first heater and a second heater having higher power consumption than the first heater, and a method for controlling same. The first heater and the second heater can be simultaneously operated to heat water and generate steam. After the steam is generated, only one of the first heater or the second heater can be operated to supply the steam to the inner case, or one of the first heater or the second heater can be operated simultaneously with a compressor.

27 Claims, 25 Drawing Sheets

(30) Foreign Application Priority Data

Feb. 25, 2022 (KR) ........................ 10-2022-0025486
Feb. 25, 2022 (KR) ........................ 10-2022-0025487

(58) Field of Classification Search
USPC ........................................................... 8/149.3
See application file for complete search history.

(56) References Cited

U.S. PATENT DOCUMENTS

| | | | |
|---|---|---|---|
| 2013/0117944 | A1 | 5/2013 | Moon et al. |
| 2017/0342651 | A1 | 11/2017 | Choi et al. |
| 2017/0364049 | A1 | 12/2017 | Yang et al. |
| 2020/0040504 | A1 | 2/2020 | Rochford et al. |
| 2021/0262149 | A1 | 8/2021 | Lee et al. |

FOREIGN PATENT DOCUMENTS

| | | | |
|---|---|---|---|
| EP | 3228742 | B1 | 6/2019 |
| JP | 2007-143735 | A | 6/2007 |
| JP | 2013-103136 | A | 5/2013 |
| JP | 2016-150040 | A | 8/2016 |
| JP | 2018-508305 | A | 3/2018 |
| JP | 2021-087512 | A | 6/2021 |
| JP | 2021-535822 | A | 12/2021 |
| KR | 10-2005-0118439 | A | 12/2005 |
| KR | 10-2007-0121970 | A | 12/2007 |
| KR | 10-0792075 | B1 | 1/2008 |
| KR | 10-2011-0035030 | A | 4/2011 |
| KR | 10-2012-0082531 | A | 7/2012 |
| KR | 10-2017-0006556 | A | 1/2017 |
| KR | 10-1780223 | B1 | 10/2017 |
| KR | 10-2018-0037459 | A | 4/2018 |
| KR | 10-2020-0021359 | A | 2/2020 |
| KR | 10-2021-0111593 | A | 9/2021 |
| RU | 2757887 | C1 | 10/2021 |
| WO | WO 2009/091169 | A2 | 7/2009 |

OTHER PUBLICATIONS

Notice of Allowance in Japanese Appln. No. 2024-544779, mailed on Jun. 3, 2025, 6 pages (with English translation).
Office Action in Australian Appln. No. 2023211955, mailed on Jun. 12, 2025, 4 pages.
Extended European Search Report in European Appin. No. 23747379.8, mailed on Feb. 25, 2025, 8 pages.
Office Action in Russian Appln. No. 2024124112, mailed on Mar. 11, 2025, 12 pages (with English translation).
Notice of Allowance in Korean Appln. No. 10-2022-0025486, mailed on Nov. 8, 2024, 2 pages (with English translation).
Notice of Allowance in Korean Appln. No. 10-2022-0025487, mailed on Nov. 8, 2024, 2 pages (with English translation).
International Search Report and Written Opinion in International Appln. No. PCT/KR2023/001260, mailed on May 15, 2023, 19 pages (with English translation).

* cited by examiner (a) (b)

(a) (b)

(a)

(a)

(b)

(a)

(a)

(a) (b)

(a)

(b)

CLOTHING TREATMENT APPARATUS AND METHOD FOR CONTROLLING CLOTHING TREATMENT APPARATUS

CROSS-REFERENCE TO RELATED APPLICATIONS

This application is a National Stage application under 35 U.S.C. § 371 of International Application No. PCT/KR2023/001260, filed on Jan. 27, 2023, which claims the benefit of Korean Application Nos. 10-2022-0025487, filed on Feb. 25, 2022, 10-2022-0025486, filed on Feb. 25, 2022, 10-2022-0013023, filed on Jan. 28, 2022, and 10-2022-0013011, filed on Jan. 28, 2022. The disclosures of the prior applications are incorporated by reference in their entirety.

TECHNICAL FIELD

The present disclosure relates to a clothing treatment apparatus and a method for controlling the clothing treatment apparatus. More specifically, the present disclosure relates to a clothing treatment apparatus and a method for controlling the clothing treatment apparatus that may spray steam onto clothes to deodorize, dry, and remove wrinkles from the clothes.

BACKGROUND

In general, a clothing treatment apparatus is a concept including a washing machine that soaks clothes in water to create a wet state and then removes foreign substances via a chemical action of detergent and a physical action such as drum rotation, and a drying machine that dries the clothes in the wet state using hot air and steam.

However, recently, a clothes care machine that keeps the clothes in a dry state pleasant and clean without soaking the clothes in water has appeared. Such clothes care machine is able to deodorize the clothes by supplying steam or hot air while the clothes are hung and to perform a refresh stroke of drying or sterilizing the clothes.

Such clothes care machine is able to selectively add fragrance to the clothes, and in recent years, has recently become an important component in the clothing treatment apparatuses alongside the washing machine and the drying machine.

Because the clothes care machine that performs the refresh stroke of the clothes accommodates therein the clothes in the dry state, a steam supply that supplies steam to the clothes is essential.

FIG. 1 shows an existing clothing treatment apparatus equipped with a steam supply.

Referring to Korean Patent Application Publication No. 10-2020-0057545, the existing clothing treatment apparatus includes a cabinet 1 forming an outer appearance thereof, and an inner casing 2 disposed inside the cabinet 1 to hang the clothes therein.

The clothing treatment apparatus may include a circulating duct 13 that is located under the inner casing 2 and circulates air in the inner casing 2, a heat exchanger 15 disposed in the circulating duct 13 to exchange heat with air, and a compressor 14 that supplies a high-temperature refrigerant to the heat exchanger 15. When the compressor 14 operates, hot air may be supplied to the inner casing 2 to increase a temperature inside the inner casing 2, and the clothes may be dried or sterilized.

In addition, the clothing treatment apparatus may include a steam tank 16 that is disposed outside the circulating duct 13 to store water therein, and a heater 17 that is accommodated in the steam tank 16 to heat water to generate steam. When the heater 17 operates, steam may be supplied into the inner casing 2 to deodorize the clothes or remove wrinkles from the clothes.

In one example, the clothes accommodated in the inner casing 2 are hung in the dry state. Therefore, for the clothes to be effectively refreshed, moisture should be supplied into the inner casing 2 in an amount sufficient to refresh the clothes.

Accordingly, the heater 17 may have a relatively great capacity such that the clothes hung in the inner casing 2 may contain a sufficient amount of moisture. For example, the heater 17 may have a greater rated capacity than a heater applied to the washing machine or the drying machine that supplies steam to the clothes in the wet state.

As a result, the existing clothing treatment apparatus has a fundamental limitation in that the heater 17 and the compressor 14 are not able to be operated simultaneously so as not to exceed an allowable rated capacity.

Therefore, when operating the heater 17 to supply steam into the inner casing 2, hot air is not able to be supplied into the inner casing 2. In other words, the steam supply is able to increase the moisture content of the clothes and raise the temperature inside the inner casing 2 to a certain level, but the temperature inside the inner casing 2 is not able to be maintained at a temperature equal to or higher than a minimum temperature required for the deodorization, the sterilization, and the drying.

As a result, when steam is supplied into the inner casing 2, there is a limit in ensuring a deodorizing and sterilizing performance of the clothes.

Moreover, the existing clothing treatment apparatus requires the supply of the sufficient amount of moisture rather than hot air to refresh the clothes, and an entirety of the supplied moisture should be dried, so that the compressor 14 should be operated after the operation of the heater 17 is completed.

As a result, in the existing clothing treatment apparatus, the temperature inside the inner casing 2 is not able to be maintained at the minimum temperature until the compressor 14 is operated, so that an effect of the refresh stroke is not exhibited.

Therefore, because the temperature inside the inner casing 2 may be raised to and maintained at the minimum temperature only at a subsequent time point when the compressor 14 is operated in the refresh stroke, there is a fundamental limitation in that the stroke itself for refreshing the clothes is inevitably delayed significantly.

In addition, at an initial time point when the compressor 14 is operated, steam is not able to be supplied into the inner casing 2, so that air in contact with the heat exchanger 15 is at a relatively low temperature. As a result, air discharged from the inner casing 2 is not able to secure enough heat to exchange heat with the refrigerant flowing through the heat exchanger 15, so that a coefficient of performance (COP) of a heat pump system is not able to be secured.

In addition, as described above, the heater 17 has the great capacity to increase the moisture content of the clothes inside the inner casing 2, so that when the heater 17 operates, humidity inside the inner casing 2 rises rapidly.

Therefore, the existing clothing treatment apparatus is not able to manage the clothes vulnerable to moisture, such as silk or cashmere.

In one example, a clothing treatment apparatus equipped with the steam supply that supplies steam to a drum where the clothes are accommodated has also appeared among the washing machines and the drying machines.

FIG. 2 shows an existing clothing treatment apparatus equipped with a steam supply that may perform drying.

Referring to Korean Patent No. 10-1448632, the existing clothing treatment apparatus may include a clothes accommodating portion 2 that is located inside the cabinet 1 to accommodate the clothes therein, a water supply pipe 5 that supplies water into the clothes accommodating portion 2, and a steam supply part 4 that is connected to the water supply pipe 5 to receive water and supply steam to the clothes accommodating portion 2.

The steam supply part 4 may be equipped with a heater 6 therein that heats water to generate steam. Accordingly, the existing clothing treatment apparatus may spray the steam into the clothes accommodating portion 2 via the steam supply part 4 during a washing stroke or a drying stroke, thereby increasing a temperature inside the clothes accommodating portion 2 to increase a washing efficiency or a drying efficiency, removing the wrinkles from the clothes, or performing the sterilization.

However, because the existing clothing treatment apparatus, such as the washing machine or the drying machine, is premised on treating the clothes in the wet state, there is no need to generate a large amount of steam inside the clothes accommodating portion 2, unlike the clothes care machine to increase the moisture content of the dry clothes.

Therefore, the existing clothing treatment apparatus shown in FIG. 2 does not need to be equipped with the large-capacity heater 6, unlike the clothes care machine.

In one example, in the existing clothing treatment apparatus, the heater 6 may be composed of a first heater 61 and a second heater 62 that may be operated independently of the first heater 61 to adjust a steam supply amount.

However, the existing clothing treatment apparatus, such as the washing machine and the drying machine, performs a dehydrating stroke or the drying stroke of removing moisture from the clothes in the wet state. Therefore, when the clothes accommodating portion 2 rotates or when the heat pump system including the compressor or a heating system (hereinafter, referred to as a heat supply) including an air heating heater is operated while performing the drying stroke, there is a fundamental limitation in that the heater 6 is not able to be operated.

As a result, even when the clothes in the dry state are put into the washing machine and the drying machine, there is a fundamental limitation in that the heater 6 and the heat supply or a motor are not able to be operated simultaneously to refresh the clothes.

Moreover, when performing the drying stroke in the clothing treatment apparatus such as the washing machine and the drying machine, because a purpose is final drying of the clothes in the wet state, even when the heater 6 is heated and supplies steam during the drying stroke, the heat supply does not stop once operation thereof begins until completion. This is because, in that case, not only does the drying performance decrease drastically, but the drying stroke is also greatly delayed.

Therefore, the washing machine and the drying machine have the limitations that there is no possibility or implication regarding a technology of simultaneously operating the heater that generate steam and the compressor, but also a technology of stopping the operation of the compressor to operate the heater that generates steam after starting the operation of the compressor.

As a result, the existing clothing treatment apparatus has a limitation in not being able to provide the technology of simultaneously operating the heater that generates steam and the compressor that generates hot air in the clothes care machine or to provide technical details on how to control and apply the heater, which is equipped as a dual heater, in the clothes care machine that treats the clothes in the dry state.

SUMMARY

Technical Problem

The present disclosure is to provide a clothing treatment apparatus that may improve a drying performance and reduce a drying stroke duration by placing a section of simultaneously operating a heater that generates steam and a compressor that heats a refrigerant.

The present disclosure is to provide a clothing treatment apparatus that may secure an initial temperature increase by placing a section of simultaneously operating a heater and a compressor before a section of drying clothes.

The present disclosure is to provide a clothing treatment apparatus that may adjust an amount of steam or an amount of power used by arranging a plurality of heaters that generate steam in a separate manner.

The present disclosure is to provide a clothing treatment apparatus that may also perform a refresh stroke such as deodorization, wrinkle removal, and drying on clothes made of a material such as silk and cashmere that are vulnerable to moisture.

Technical Solutions

To solve the above-mentioned problems, the present disclosure provides a clothing treatment apparatus in which a heater assembly includes a plurality of heaters that generate steam and are able to be controlled independently of each other.

The plurality of heaters may operate in a manner of dividing a maximum amount of heater power allocated to the heater assembly.

The plurality of heaters may include a first heater and a second heater, and the first heater and the second heater may simultaneously operate to heat water and generate steam. However, after steam is generated, one of the first heater and the second heater may operate to supply steam to the inner casing.

Allowable amount of power of the clothing treatment apparatus may be set to be smaller than an amount of power required when the first heater, the second heater, and the compressor operate simultaneously, and may be set to be greater than an amount of power required when the compressor and one of the first heater and the second heater operate simultaneously.

The preheating step may include a section where the compressor and one of the first heater and the second heater simultaneously operate.

The preheating step may include a first section where the compressor and one of the first heater and the second heater simultaneously operate, and a second section where only the compressor operates.

The second heater may generate more steam than the first heater, and the preheating step may include operating the second heater and stopping the operation of the first heater.

The second heater may be controlled to repeat the operation and stopping in the preheating step.

An operation duration of the second heater may be set to be greater than a stopping duration in the preheating step.

When one of a discharge pressure of the refrigerant from the compressor, a temperature of the refrigerant, and a temperature inside the inner casing is greater than a reference value, the second heater may be controlled to stop operating in the preheating step.

The second heater may generate more steam than the first heater, and the preheating step may include operating the first heater and stopping the operation of the second heater.

An operation duration of the first heater may be set to be greater than an OFF duration of the first heater in the preheating step.

The first heater and the second heater that generate steam may simultaneously operate to supply steam to the inner casing.

The operation of the compressor may be stopped when simultaneously operating the first heater and the second heater.

The operation of the compressor, the first heater, and the second heater may be stopped for a set time period by simultaneously operating the first heater and the second heater.

The clothing treatment apparatus may further include a blowing fan that supplies air that has passed through the heat exchanger into the inner casing, and the blowing fan may be operated after being stopped for a set time period but the operation of the compressor may be stopped.

When hot air is supplied to the clothes by operating the compressor, the operation of the first heater and the second heater may be stopped.

In one example, when the clothes are vulnerable clothes, only one of the first heater and the second heater may be operated when supplying steam.

The clothing treatment apparatus may further include a clothes setter that receives vulnerability information indicating that the clothes accommodated in the inner casing are able to be deformed by moisture or high temperature, and when the vulnerability information is input, a section where the heater and the compressor simultaneously operate may be skipped.

Only one of the first heater and the second heater may be operated when the vulnerability information is input.

The clothing treatment apparatus may include a blowing fan that supplies air that has passed through the heat exchanger into the inner casing, and the blowing fan may be operated and the operation of the compressor may be stopped after the drying of the clothes when the vulnerability information is input.

The vulnerability information may include cashmere information indicating that the clothes at least partially include a cashmere material, and the second heater may be operated when the cashmere information is input.

The second heater may generate more steam than the first heater, the vulnerability information may include silk information indicating that the clothes at least partially include a silk material, and the first heater may be operated when the silk information is input.

The second heater may generate more steam than the first heater, the vulnerability information may include silk information indicating that the clothes at least partially include a silk material, and steam may be sprayed when the silk information is input.

The present disclosure may perform sterilization by operating the first heater and the compressor.

When performing the sterilization, the first heater and the compressor may simultaneously operate.

When performing the sterilization, the first heater may be controlled to repeat operating and stopping.

When performing the sterilization, the operation of the first heater may be stopped when the temperature inside the inner casing increase to a temperature equal to or higher than a target temperature, and the first heater may be operated when the temperature inside the inner casing falls to a temperature equal to or lower than the sterilization temperature.

Advantageous Effects

The present disclosure may further shorten the execution duration of the course of treating the clothes.

The present disclosure may further ensure the durability of the clothes by reducing the time period during which the clothes are affected by heat and moisture.

The present disclosure may improve the drying performance and reduce the drying stroke duration by placing the section of simultaneously operating the heater that generates steam and the compressor that heats the refrigerant.

The present disclosure may secure the initial temperature increase by placing the section of simultaneously operating the heater and the compressor before the section of drying the clothes.

The present disclosure may adjust the amount of steam or the amount of power used by arranging the plurality of heaters that generate steam in the separate manner.

The present disclosure may also perform the refresh stroke such as the deodorization, the wrinkle removal, and the drying on the clothes made of the material such as the silk and the cashmere that are vulnerable to moisture.

BEST MODE

Figure 1:
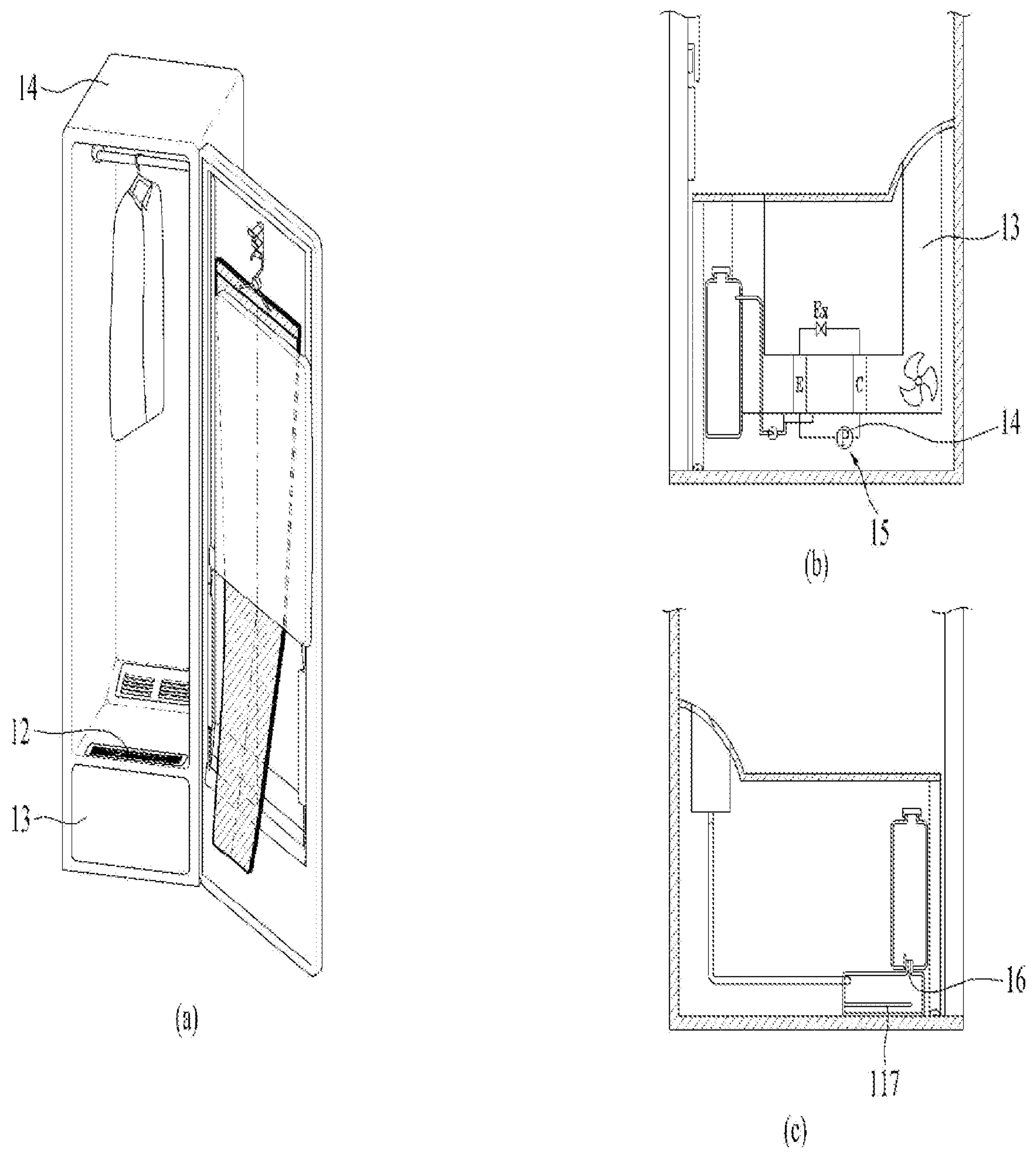
FIG. 1 shows an existing clothing treatment apparatus.
Figure 2:
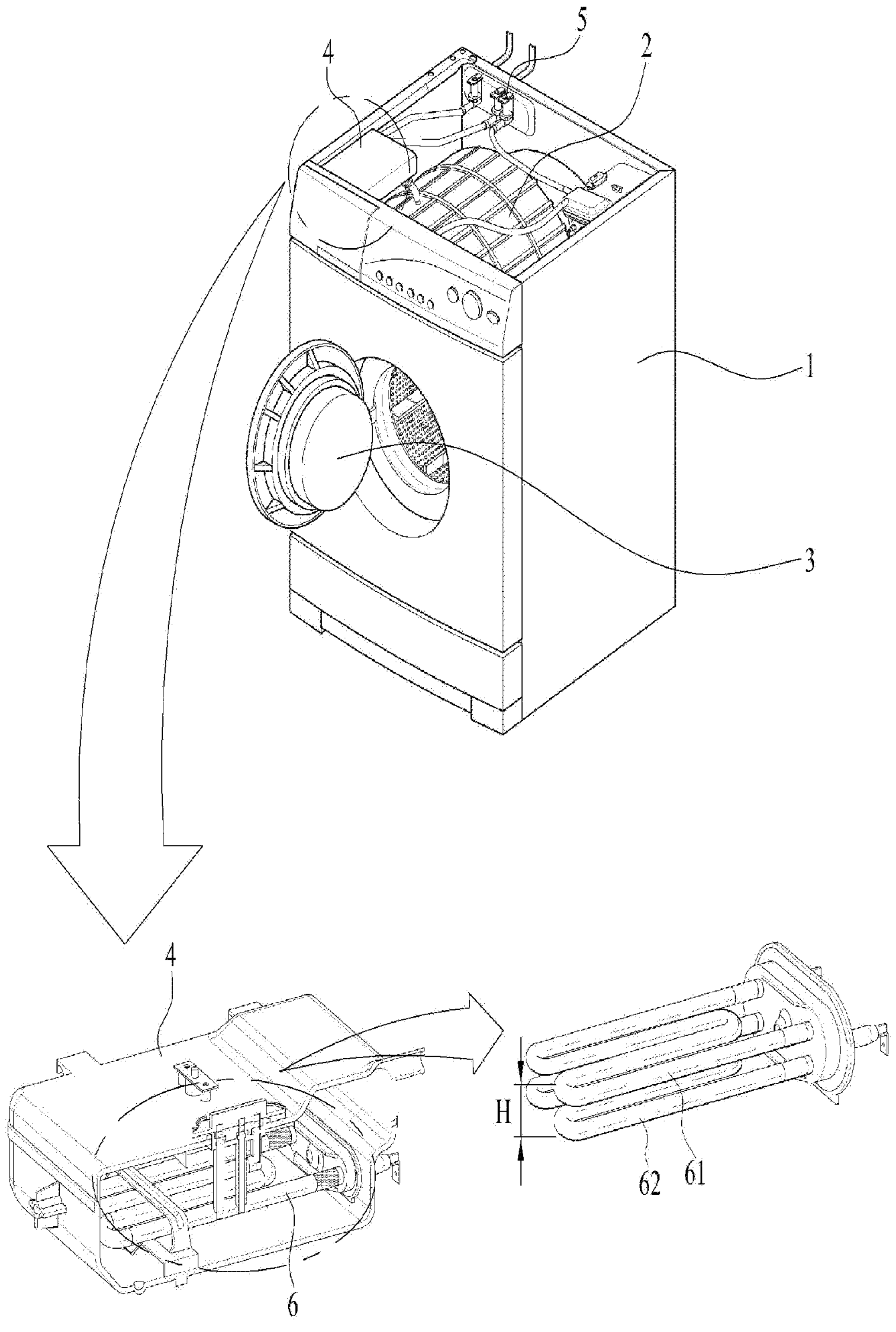
FIG. 2 shows another existing clothing treatment apparatus.

Hereinafter, embodiments disclosed herein will be described in detail with reference to the attached drawings. In the present document, the same or similar reference numerals will be assigned to the same or similar components even in different embodiments, and descriptions thereof will be replaced with the first description. As used herein, a singular expression includes a plural expression unless the context clearly dictates otherwise. Additionally, in describing the embodiments disclosed herein, when it is determined that a detailed description of a related known technology may obscure the gist of the embodiments disclosed herein, the detailed description will be omitted. In addition, it should be noted that the attached drawings are only for easy understanding of the embodiments disclosed herein and should not be construed as limiting the technical idea.

Figure 3:
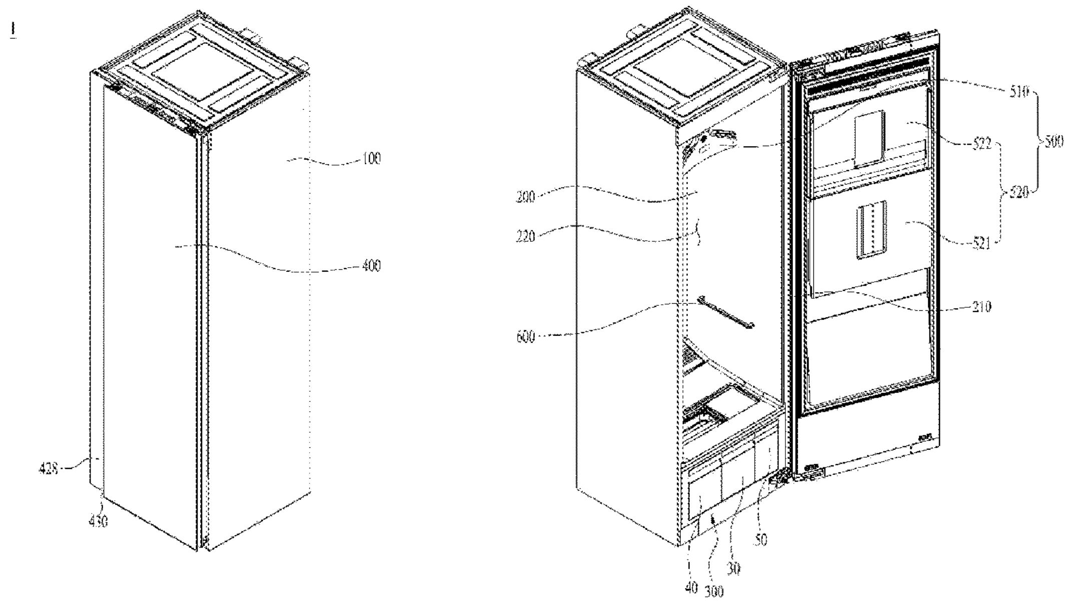
FIG. 3 shows an outer appearance of a clothing treatment apparatus according to the present disclosure.

FIG. 3 shows an outer appearance of a clothing treatment apparatus 1 according to the present disclosure.

Referring to (a) in FIG. 3, the clothing treatment apparatus according to the present disclosure may include a cabinet 100 that forms an outer appearance thereof, and a door 400 that is pivotably coupled to the cabinet 100.

The door 400 may include a main body 410 that forms a front surface of the cabinet 100, and an installation body 420 extending from one side of the main body 410 and on which a display to display information of the clothing treatment apparatus may be installed.

The installation body 420 may form a step 430 from the main body 410 toward a rear side of the cabinet 100.

In one example, at least a portion of the installation body 420 may be disposed at the rear of the main body 410 so as to overlap the main body 410 in a front and rear direction. Accordingly, the step 430 may perform a role of a handle.

The installation body 420 may be made of a material different from that of the main body 410 or may have a color different from that of the main body 410. Additionally, the installation body 420 may be made of a translucent material that allows light emitted from the display to pass therethrough.

Referring to (b) in FIG. 3, an inner casing 200 having an accommodating space 220 for accommodating clothes may be disposed inside the cabinet 100. The inner casing 200 may have an opening 210 defined in a front surface thereof through which the clothes enter and exit, and the opening 210 may be shielded by the door 400.

The inner casing 200 may be made of a plastic resin, and may be made of a reinforced plastic resin that is not deformed by air at a temperature higher than a room temperature or heated air (hereinafter, referred to as hot air), steam, or moisture.

The inner casing 200 may have a height greater than a width. As a result, the clothes may be accommodated in the accommodating space 220 without being folded or wrinkled.

The clothing treatment apparatus 1 according to the present disclosure may include a hanger assembly 500 for the clothes to be hung in the accommodating space 220 of the inner casing 200.

The hanger assembly 500 may include a hanger 510 disposed on a top surface of the inner casing 200 to hang the clothes.

When the clothes are hung on the hanger 510, the clothes may be placed suspended in air within the accommodating space 220.

In one example, the hanger assembly 500 may further include a presser assembly 520 coupled to an inner surface of the door 400 to fix the clothes.

The hanger 510 may be formed in a shape of a bar disposed along a width direction of the inner casing 200 to support a clothes hanger on which the clothes are hung. Additionally, as shown, the hanger 510 may be formed in a shape of the clothes hanger, so that the clothes may be directly hung thereon.

The clothing treatment apparatus according to the present disclosure may further include a vibrator that may remove foreign substances such as fine dust attached to the clothes by vibrating the hanger 510.

The hanger assembly 500 may include the presser assembly 520 disposed on the door 400 to press and fix the clothes. The presser assembly 520 may include a support 522 that is fixed to the inner surface of the door 400 and supports one surface of the clothes, and a presser 521 that presses the clothes supported on the support 522.

The presser 521 may move toward or away from the support 522. For example, the presser 521 may be pivotably disposed on the support 522 or the inner surface of the door 400.

Accordingly, the presser 521 and the support 522 may press both surfaces of the clothes to remove wrinkles from the clothes and create intended creases.

The clothing treatment apparatus according to the present disclosure may have a machine room 300 in which various apparatuses that may supply one or more of hot air and steam to the accommodating space 220 or purify or dehumidify outdoor air of the cabinet 100 are installed.

The machine room 300 may be defined separately or partitioned from the inner casing 200, but may be in communication with the inner casing 200.

The machine room 300 may be defined under the inner casing 200. Accordingly, when hot air and steam with small specific gravities are supplied to the inner casing 200, hot air and steam may be naturally supplied to the clothes.

The machine room 300 may include a heat supply part 340 that may supply hot air into the inner casing 200. The heat supply part 340 may be formed as a heat pump system or as a heater that directly heats air with electrical energy.

When the heat supply part 340 is formed as the heat pump system, the heat supply part 340 may dehumidify and heat air discharged from the inner casing 200 again and supply air to the inner casing 200. A detailed structure thereof will be described later.

The machine room 300 may include a steam supply part 800 that may supply steam into the inner casing 200. The steam supply part 800 may directly supply steam into the inner casing 200. A detailed structure thereof will be described later.

To this end, the inner casing 200 may include a plurality of through-holes 230 that extend through one surface thereof to be in communication with the machine room 300.

Air from the accommodating space 220 may be supplied to the machine room 300 via the through-holes 230, and one or more of hot air and steam generated in the machine room 300 may be supplied to the accommodating space 220.

The through-holes 230 may include an inlet hole 231 extending through a bottom surface of the inner casing 200 and through which air inside the inner casing 200 is discharged to or sucked into the machine room 300, and an outlet hole 232 extending through the bottom surface of the inner casing 200 and through which hot air generated in the machine room 300 is discharged.

The outlet hole 232 may be defined in the bottom surface of the inner casing 200 biased toward a rear surface of the inner casing 200. For example, the outlet hole 232 may be defined between the bottom surface and the rear surface of the inner casing 200 at an angle to the ground and facing the hanger 510.

Additionally, the inlet hole 231 may be defined in the bottom surface of the inner casing 200 biased toward a front side. Accordingly, the inlet hole 231 may be defined to be spaced apart from the outlet hole 232.

The through-holes 230 may include a steam hole 233 through which steam generated by the steam supply part 800 is supplied. The steam hole 233 may be defined on one side of the outlet hole 232.

In one example, at the front side of the machine room 300, a water supply tank 30 that may supply water to the steam supply part 800 and a water drainage tank 40 in which condensed water condensed in the heat supply part 340 is collected may be disposed.

The water supply tank 30 and the water drainage tank 40 may be detachably disposed at the front side of the machine room 300. Accordingly, the clothing treatment apparatus 1 according to the present disclosure may be freely installed regardless of a water source or a drain.

In one example, at the front side of the machine room 300, a drawer 50 that is extended and retracted in the front and rear direction and has a separate accommodating space may be further disposed. The drawer 50 may store a steam generator or an iron therein.

Figure 4:
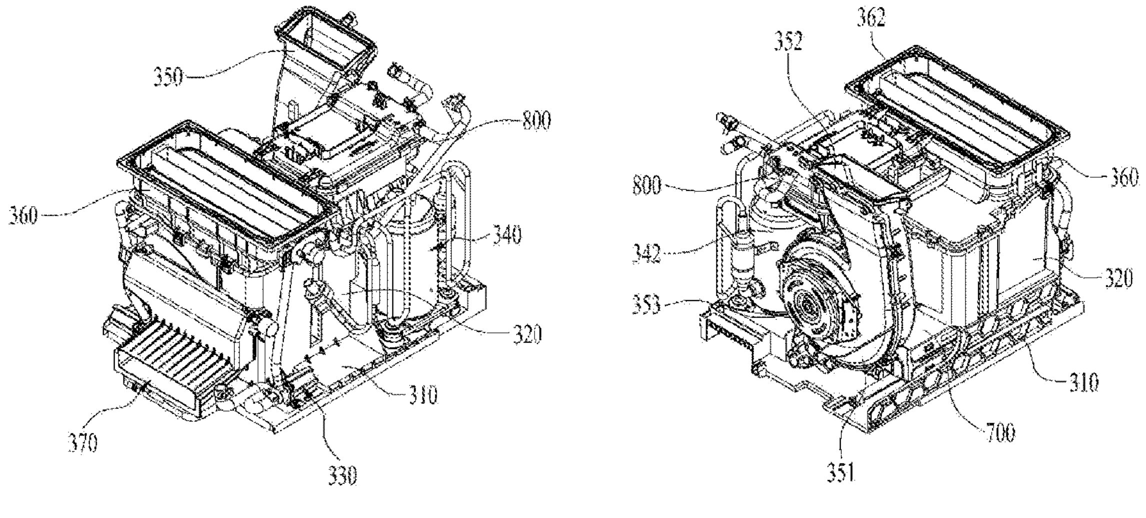
FIG. 4 shows a structure of a machine room of a clothing treatment apparatus according to the present disclosure.

FIG. 4 shows a structure of a machine room of a clothing treatment apparatus according to the present disclosure.

(a) in FIG. 4 is a front view of the machine room 300, and (b) in FIG. 4 is a rear view of the machine room 300.

Inside the machine room 300, components to supply hot air to a clothes treating space, to circulate air inside the clothes treating space, to supply steam to the clothes treating space, or to clean air outside the cabinet may be disposed.

The machine room 300 may include a base 310 on which a space to support various devices or to install the various devices is defined. The base 310 may provide an area where the various devices are installed.

The base 310 may be equipped with a circulating duct 320 through which air introduced from the inner casing 200 or outside the cabinet 100 flows.

The circulating duct 320 may be formed in a shape of a casing with an open top surface, and some components of the heat supply part 340 may be installed inside the circulating duct 320.

When the heat supply part 340 is formed as the heat pump system, the heat supply part 340 may include, inside the circulating duct 320, heat exchangers 341 and 343, which will be described later, and a compressor 342 that supplies a high-temperature and high-pressure refrigerant to the heat exchanger.

The heat exchangers 341 and 343 may be accommodated inside the circulating duct 320 and cool and dehumidify air flowing through the circulating duct 320 or heat the air to generate hot air.

When the circulating duct 320 is constructed to suck air outside the cabinet 100, an outdoor air duct 370 that sucks outdoor air may be installed in front of the circulating duct 320.

The circulating duct 320 may be in communication with the outside air duct 370 and may selectively suck outdoor air.

The water supply tank and the water drainage tank may be detachably coupled to a front surface of the circulating duct 320. The water supply tank 30 and the water drainage tank 40 may be seated on the outdoor air duct 370.

The circulating duct 320 may be coupled to the base 310 or may be integrally formed with the base 310. For example, the base 310 and the circulating duct 320 may be manufactured via injection molding.

The machine room 300 may include a base cover 360 that allows the circulating duct 320 and the inlet hole 231 to be in communication with each other.

The base cover 360 may be coupled to an upper portion of the circulating duct 320 and may guide air sucked from the inlet hole 231 into the circulating duct 320.

The base cover 360 may block air inside the circulating duct 320 from being discharged to the outside by shielding a top surface of the circulating duct 320. A lower portion of the base cover 360 and the top surface of the circulating duct 320 may form one surface of a flow channel of the circulating duct 320.

The base cover 360 may include an inlet 362 that connects the inlet hole 231 and the circulating duct 320 to each other. The inlet 362 may be formed in a duct shape and may serve as an intake duct that delivers air inside the inner casing 200 to the circulating duct 320.

The machine room 300 may be installed with the steam supply part 800 that generates steam by being connected to the water supply tank 30 to receive water, and supplies steam to the inner casing 200. The steam supply part 800 may be seated on the base cover 360.

The steam supply part 800 may be disposed at the rear of the inlet 362.

The machine room 300 may include a fan installation portion 350 disposed to allow the circulating duct 320 and the inner casing 200 to be in communication with each other. The fan installation portion 350 may include a blowing fan 353 that provides power for air inside the circulating duct 320 to flow in one direction, and a fan housing 351 that accommodates the blowing fan 353 therein and is coupled to or extends from the circulating duct 320.

The fan installation portion 350 may have a discharge duct 352 that allows the circulating duct 320 and the outlet hole 232 to be in communication with each other.

The discharge duct 352 may be constructed such that a cross-section thereof extends from the fan housing 351 toward the outlet hole 232 with an area size corresponding to that of the outlet hole 232.

As a result, air inside the inner casing 200 may be introduced via the base cover 360, pass through the circulating duct 320, and then be supplied back into the inner casing 200 via the fan installation portion 350.

In one example, the base 310 may have a compressor installation portion 313 where the compressor 342, which supplies the refrigerant to the heat exchangers 341 and 343, is installed. The compressor installation portion 313 may be disposed outside the circulating duct 320.

Additionally, the base 310 may be installed with a controller or control panel 700 that controls the clothing treatment apparatus according to the present disclosure.

The base 310 may have a controller installation portion 312 that defines a space into which the controller 700 may be inserted under the circulating duct 320.

The controller 700 may control all electronically controlled components, such as the compressor 342, the steam supply part 800, and the blowing fan 353.

Because the controller 700 is inserted into and supported in the base 310, vibration or impact applied to the controller 700 may be cushioned. Additionally, because the controller 700 is disposed close to all of the electronic components, occurrence of a control error such as noise may be minimized.

Additionally, the steam supply is disposed on the circulating duct 320, and the controller 700 is disposed under the circulating duct 320. Therefore, the circulating duct 320 may be formed in a shape of a straight duct between the steam supply part 800 and the controller 700. Therefore, an airflow resistance of air passing through the circulating duct 320 may be minimized.

The circulating duct 320, the outdoor air duct 370, the steam supply part 800, the controller 700, and the heat supply part 340 may be formed on the base 310 in a module format.

As a result, the base 310 may be easily installed and maintained by being extended forward from and retracted rearward into the machine room 300.

Figure 5:
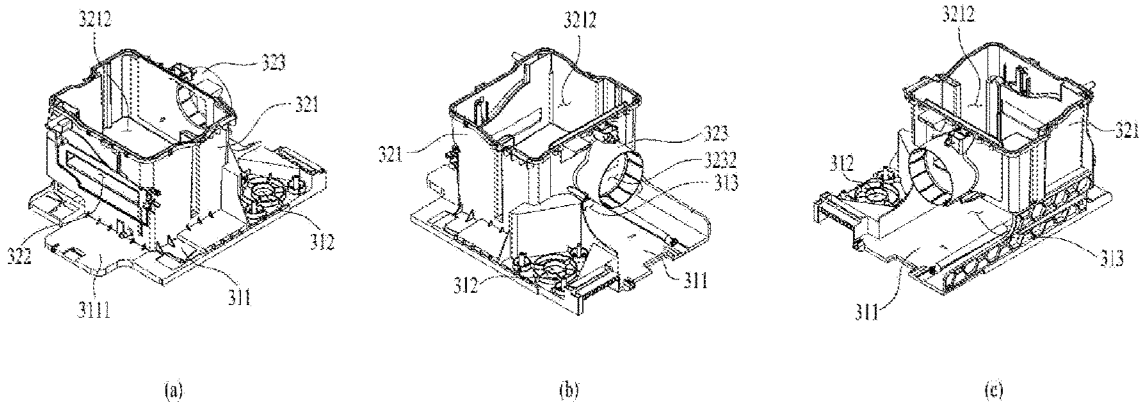
FIG. 5 shows a structure of a base of a machine room of a clothing treatment apparatus according to the present disclosure.

FIG. 5 shows a structure of a base of a machine room of a clothing treatment apparatus according to the present disclosure.

(a) in FIG. 5 is a front perspective view of the base 310, and (b) and (c) in FIG. 5 are rear perspective views of the base 310.

The base 310 may be installed on a base plate forming a bottom surface of the clothing treatment apparatus. The base 310 may itself form the bottom surface of the clothing treatment apparatus.

The base 310 may include a base bottom 311 forming a support surface. The base bottom 311 may form the bottom surface of the clothing treatment apparatus. Additionally, the base bottom 311 may be installed on a top surface of a bottom surface of the cabinet 100, which forms the bottom surface of the clothing treatment apparatus.

The base 310 may be integrally formed with the circulating duct 320, which forms at least a portion of a flow channel through which air flows. The circulating duct 320 may be formed to extend upward from the base bottom 311.

The circulating duct 320 may include a duct body 321 extending from the base bottom 311 to form the flow channel, a heat exchanger installation portion 3212 that provides a space for the evaporator 341 or the condenser 343 to be installed inside the duct body 321, and an air outlet 323 disposed at the rear of the duct body 321 and through which air of the duct body 321 is discharged.

The air outlet 323 may be formed in a shape of a pipe extending rearward from the duct body 321. A diameter of the air outlet 323 may be smaller than a width of the duct body 321.

The air outlet 323 may be connected to a fan housing 351. Air discharged from the air outlet 323 may be guided into the inner casing 200 via the fan housing 351.

The circulating duct 320 may include an outdoor air inlet 322 defined through a front surface of the duct body 321.

The outdoor air inlet 322 may be in communication with the outdoor air duct 370. The outdoor air duct 370 may be seated and supported in front of the outdoor air inlet 322.

The circulating duct 320 may include a damper that opens and closes the outside air inlet 322. By opening and closing the damper, outdoor air may be allowed to be introduced into the circulating duct 320 or blocked from being introduced into the circulating duct 320.

The base 310 may include the compressor installation portion 312 that provides the space where the compressor 342 is installed. The compressor installation portion 312 may be formed at one side of the base bottom 311, and may be formed integrally with the base bottom 311.

The compressor installation portion 312 may have a protrusion that may support the compressor 342. The compressor installation portion 312 may be disposed biased toward a rear side of the base 310. The compressor installation portion 312 may be disposed such that at least a portion thereof overlaps the air outlet 323 in a width direction.

A buffer member that reduces vibration transmitted from the compressor 342 may be installed in the compressor installation portion 312. The buffer member may be fixed to the protrusion.

The base 310 may include the controller installation portion 313 where the controller 700 is installed. The controller installation portion 313 may be formed between the base bottom 311 and the circulating duct 320. The controller installation portion 313 may be formed between the base bottom 311 and a bottom surface of the circulating duct 320. The controller installation portion 313 may be formed in a duct shape that is open at one of a front side and a rear side at a location under the circulating duct 320.

A structure of the controller installation portion 313 will be described later.

Figure 6:
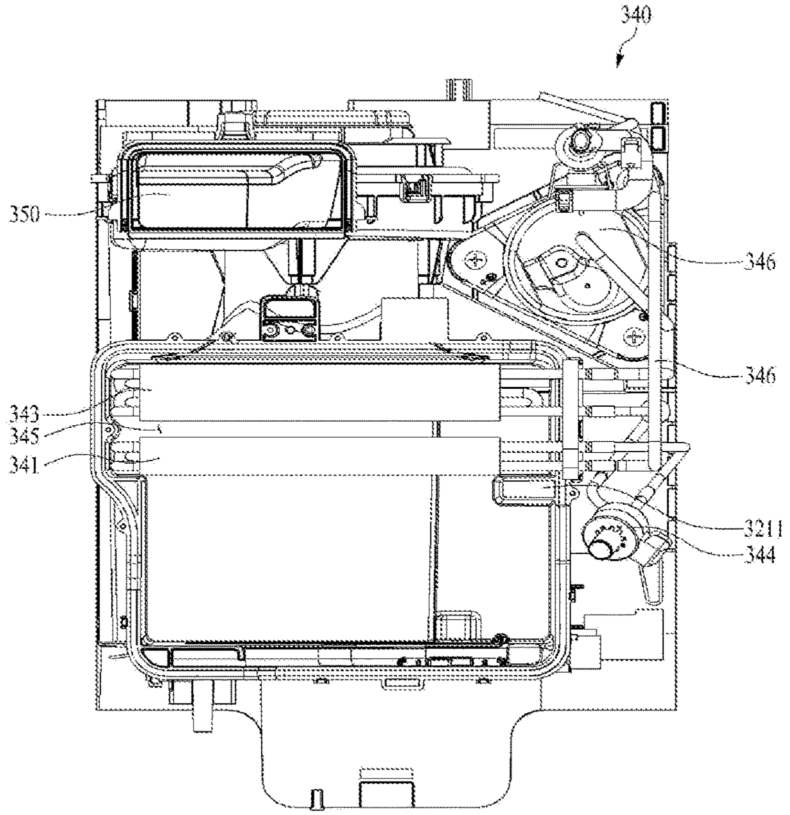
FIG. 6 shows a structure of a circulating duct of a clothing treatment apparatus according to the present disclosure.

FIG. 6 shows a structure of a circulating duct of a clothing treatment apparatus according to the present disclosure.

The circulating duct 320 may extend upward from the base bottom to form the flow channel through which air flows. The circulating duct 320 may include the heat exchanger installation portion 3212 that provides the space where the evaporator 341 and the condenser 343 are installed. The heat exchanger installation portion 3212 may be disposed inside the duct body 321.

The duct body 321 may have an open top surface. The condenser 343 and the evaporator 341 may be inserted and installed via the opening of the duct body 321.

The opening of the duct body 321 may be shielded by the base cover 360, and the base cover 360 and the duct body 321 may form the flow channel of the circulating duct 320.

The front surface of the duct body 321 may be disposed to be spaced rearwardly apart from a front end of the base bottom 311.

As a result, the base bottom 311 may secure a support surface 3111 on which one or more of the water supply tank 30 or the water drainage tank 40 and the outdoor air duct 370 are installed and supported.

In one example, the heat supply part 340 may include the evaporator 341 that is installed inside the circulating duct 320 and is formed as a heat exchanger that cools and dehumidifies air introduced into the circulating duct 320, the condenser 343 that is formed as a heat exchanger that heats air that has passed through the evaporator 341 to generate hot air, the compressor 342 that supplies the refrigerant that exchanges heat with air to the condenser 343 and is disposed outside the circulating duct 320, and an expansion valve 344 that expands and cools the refrigerant that has passed through the condenser 343.

In one example, as the duct body 321 is integrally molded with the base 310, a vertical dimension of the heat exchanger installation portion 3212 may also be more secured, and vertical dimensions of the condenser 343 and the evaporator 341 may also be increased.

As a result, widths in the front and rear direction of the condenser 343 and the evaporator 341 may be reduced, so that the number of refrigerant pipes passing through the condenser and the evaporator may be reduced. Accordingly, a flow loss of air passing through the condenser and the evaporator may be reduced.

In one example, a sum of a length of the evaporator 341 and a length of the condenser 343 may be smaller than a length of the heat exchanger installation portion 3212. Accordingly, the length in the front and rear direction of the heat exchanger installation portion 3212 may be equal to or smaller than half the length of the duct body 321.

Therefore, because the heat exchanger installation portion 3212 may be sufficiently spaced apart from the outdoor air inlet 322, a sufficient space for outdoor air and air inside the inner casing 200 to be introduced may be secured inside the circulating duct 320.

In one example, the interior of the duct body 321 may include an installation partition wall 3211 that separates the heat exchanger installation portion 3212 from the outside of the installation portion 3212 during heat exchange. The installation partition wall 3211 may protrude from a side surface of the duct body 321 and support a front side of the evaporator 341.

Additionally, the duct body 321 may be expanded in width based on the installation partition wall 3211 and extend rearward.

As a result, a width of the heat exchanger installation portion 3212 may be greater than half the width of the base 310. Additionally, a width of the circulating duct 320 may be greater than half the width of the base 310.

A width of the condenser 343 and a width of the evaporator 341 may also be greater than half the total width of the base 310.

As described above, when the widths of the condenser 343 and the evaporator 341 are secured, a heat exchange capacity may be sufficiently secured.

Additionally, the fan housing 351 may be disposed to overlap the condenser 343 or the evaporator 341 in the front and rear direction. Therefore, air that has passed through the evaporator 341 and the condenser 343 may flow into the fan housing 351 without bending of the flow channel. In other words, air introduced into the circulating duct 320 may minimize a flow loss because there is no bending of the flow channel in the process of flowing to the fan housing.

Figure 7:
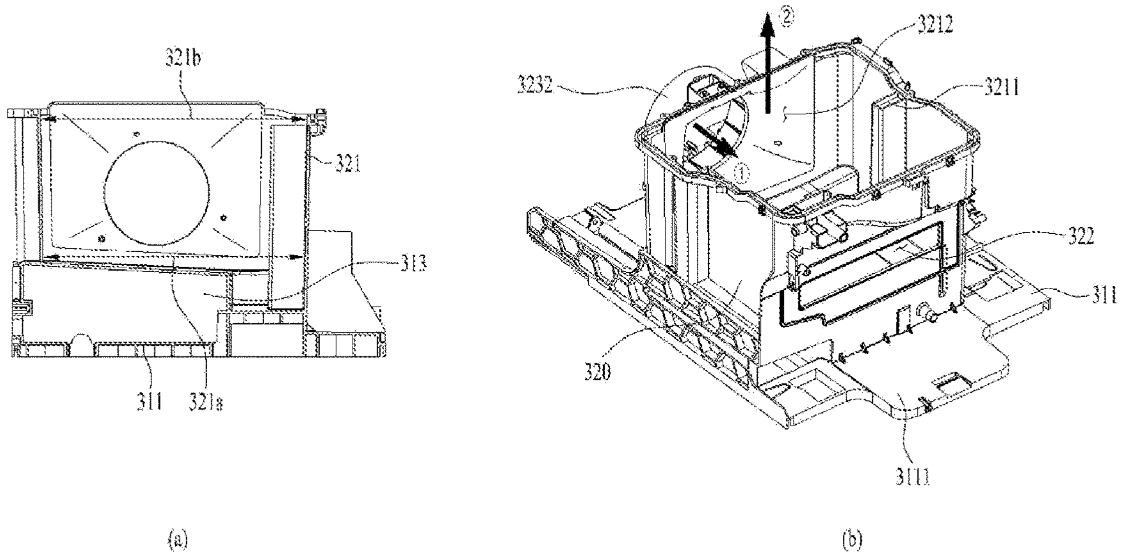
FIG. 7 illustrates a shape of a circulating duct of a clothing treatment apparatus according to the present disclosure.

FIG. 7 illustrates a shape of a circulating duct of a clothing treatment apparatus according to the present disclosure.

On the base 310, the base bottom 311 and the circulating duct 320 may be integrally molded via mold injection.

A mold for forming an inner surface of the duct body 321 may be removed by being withdrawn upward from the inside of the duct body 321. In this regard, to facilitate the withdrawal of the mold, a wall surface of the duct body 321 may be inclined at a predetermined angle with respect to a direction of removal of the mold.

A width of a bottom surface 321*a* of the duct body 321 may be greater than a width of a top surface 321*b* of the duct body 321.

Specifically, a distance between wall surfaces of the duct body 321 facing each other may be increased as a distance from the base bottom 311 increases. A distance between left and right side surfaces of the circulating duct facing each other may be increased along the withdrawal direction of the mold. Accordingly, the removal of the mold may be facilitated.

In one example, the air outlet 323 may include an air extending pipe 3231 extending from a rear side of the duct body 321 such that a diameter or a width thereof decreases, and an air discharge pipe 3232 that extends in a pipe shape with a uniform diameter from the air extending pipe 3231 and defines a hollow 3233 therein. The air extending pipe 3231 may perform a function of a nozzle and thus increase a speed of discharged air.

Additionally, a mold for forming the air outlet 323 may be removed as shown in the drawing above. The mold may be withdrawn forward from the inside of the air outlet 323 toward the inside of the circulating duct 320 and then removed toward the open top surface of the circulating duct 320. The mold may be formed in a structure that facilitates the withdrawal thereof in such process.

Figure 8:
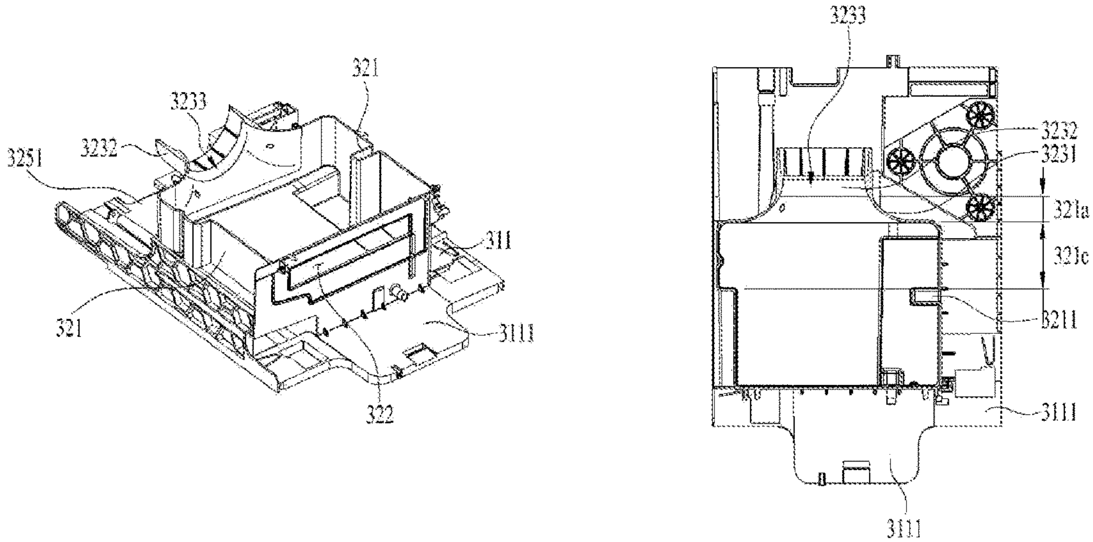
FIG. 8 shows a cross-sectional view of the circulating duct.

FIG. 8 shows a cross-sectional view of the circulating duct.

The installation partition wall 3211 may protrude inward from an inner wall of the duct body 321 or may be formed as an outer wall of the circulating duct is recessed inward.

The heat exchanger installation portion 3212 may be formed between the heat exchanger installation partition wall 3211 and the air outlet 323.

The mold for forming the air outlet 323 may be withdrawn forwardly of the air outlet 323 and then withdrawn upward to be removed. When the mold for forming the air outlet 323 is withdrawn forward from inside the air outlet 323, it is necessary to prevent the mold from interfering with the heat exchanger installation partition wall. To this end, a design numeric value of the air outlet 323 may be adjusted.

Specifically, when molding the air outlet 323, a mold for molding a front side and a mold for molding a rear side based on a parting line 3233 of the air outlet 323 in the drawing may be separately disposed. Accordingly, directions of removal of the molds may also be different from each other. The mold for molding a portion positioned at the front with respect to the parting line of the air outlet 323 may be withdrawn forward, and the mold for molding a portion positioned at the rear with respect to the parting line of the air outlet 323 may be withdrawn rearward.

That is, to prevent the mold that is withdrawn forward from interfering with the heat exchanger installation partition wall during the withdrawal process, a distance 1 321*a* may be smaller than a distance 2 321*c* in the drawing. The distance 1 321*a* may refer to a distance between the parting line of the air outlet 323 and a front end of the air outlet 323. Additionally, the distance 1 321*a* may refer to a distance between the parting line of the air outlet 323 and a rear opening of the circulating duct. The distance 2 321*c* may refer to a distance between the front end of the air outlet 323 and the heat exchanger installation partition wall. Additionally, the distance 2 321*c* may refer to a distance between the rear opening of the circulating duct and the heat exchanger installation partition wall 3211.

Figure 9:
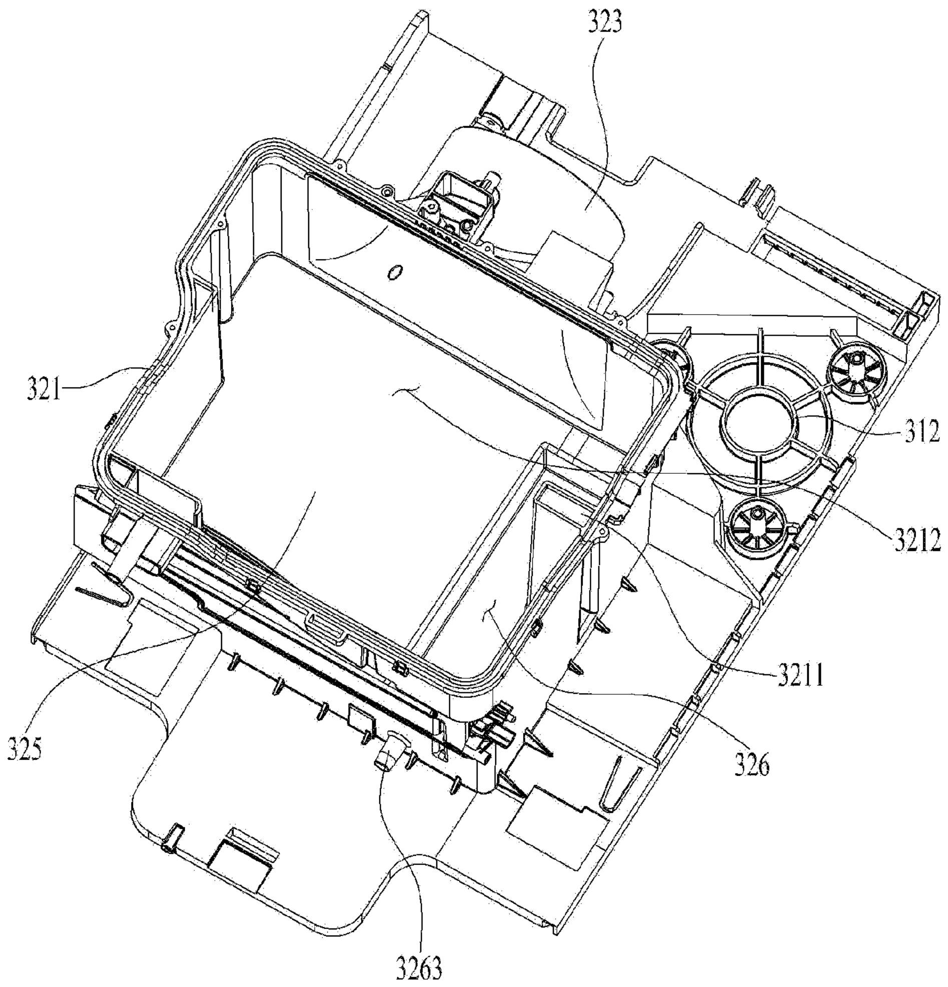
FIG. 9 shows in detail a structure of a water reservoir of a clothing treatment apparatus according to the present disclosure.

FIG. 9 shows in detail a structure of a water reservoir of a clothing treatment apparatus according to the present disclosure.

When the compressor 342 and the blowing fan 353 operate in the clothing treatment apparatus according to the present disclosure, air supplied from the outside of the cabinet 100 and air supplied from the inner casing 200 are cooled while passing through the evaporator 341, and water vapor contained in the air condenses.

Water condensed in the evaporator 341 may accumulate on the bottom surface of the circulating duct 320.

The clothing treatment apparatus according to the present disclosure may include a water reservoir 326 formed as a portion of the bottom surface of the duct body 321 is recessed to collect condensed water condensed in the evaporator 341.

The water reservoir 326 is a space defined as the bottom surface of the duct body 321 is recessed, and is able to form one side surface of the controller installation portion 313.

The water reservoir 326 may be formed to be recessed downward from the bottom surface of the circulating duct 320.

The water reservoir 326 may be formed integrally with the circulating duct 320. While injection molding the circulating duct 320 on the base 310, a portion of the bottom surface of the circulating duct 320 may be molded to be recessed to create the water reservoir 326.

At least a portion of a top surface of the water reservoir 326 may be disposed parallel to the heat exchanger installation portion 3212.

The base 310 may include a drainage pipe 3263 that discharges water collected in the water reservoir 326 to the outside.

The drainage pipe 3263 may protrude from a lower portion of the water reservoir 326 to the outside of the circulating duct 320. The drainage pipe 3263 may discharge water stored in the water reservoir to the outside of the base. As a result, water collected in the water reservoir 326 may be prevented from spoiling or flowing back to the bottom surface of the circulating duct 320.

The circulating duct 320 includes the partition wall 3211 extending from the inner surface of the duct body 321. The partition wall 3211 may protrude inward from an inner wall of the circulating duct 320, or the outer wall of the circulating duct 320 may be recessed inward and protrude inward. The partition wall 3211 may guide locations where the heat exchangers 341 and 343 are installed, and may prevent air entering the heat exchanger from passing by bypassing the heat exchanger.

The partition wall 3211 may be disposed in the water reservoir 326.

Figure 10:
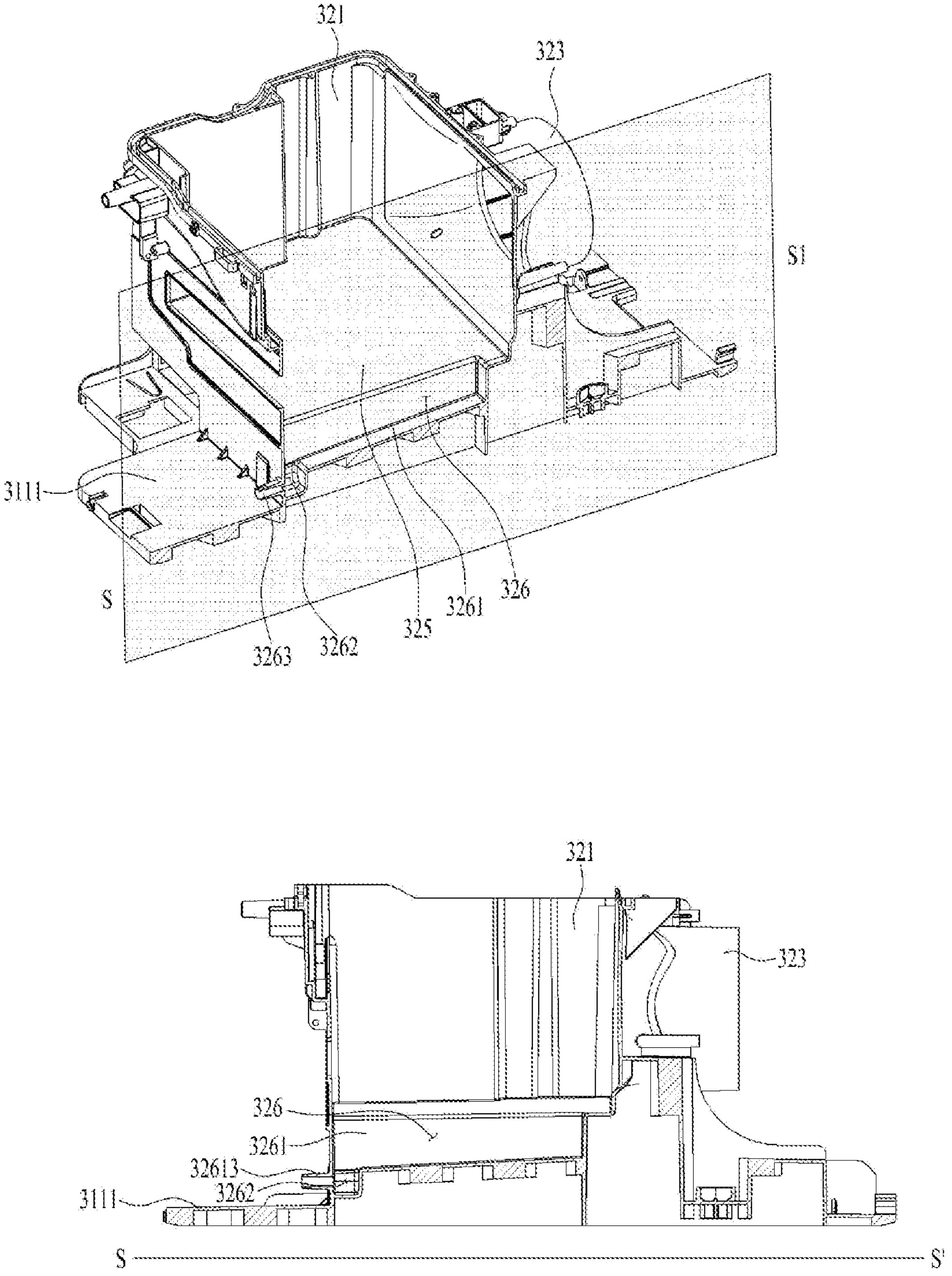
FIG. 10 shows a cross-sectional view S-S' of the circulating duct cut in a height direction.

FIG. 10 shows a cross-sectional view S-S' of the circulating duct cut in a height direction.

The water reservoir 326 may include a bottom surface 3261 on which water accumulates, and a recessed portion 3262 that is recessed further downward from the bottom surface 3261. The drainage pipe 3263 may be disposed on an outer surface of the circulating duct 320 at a position corresponding to the recessed portion 3262. As a result, the drainage pipe 3263 may be disposed on a portion of the water reservoir 326 with the lowest water level. Water collected in the water reservoir 326 may flow to the drainage pipe 3263 by a self-weight thereof.

Figure 11:
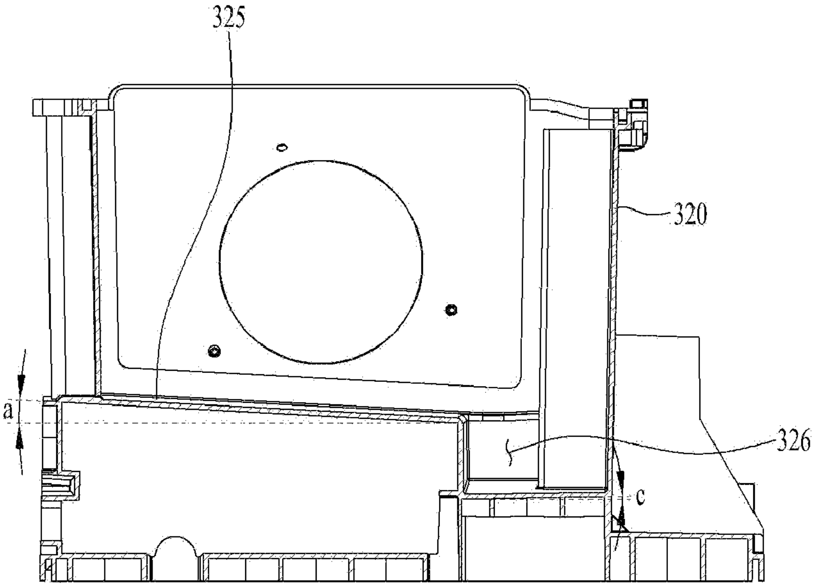
FIG. 11 shows an inclined structure related to the water reservoir.
Figure 11:
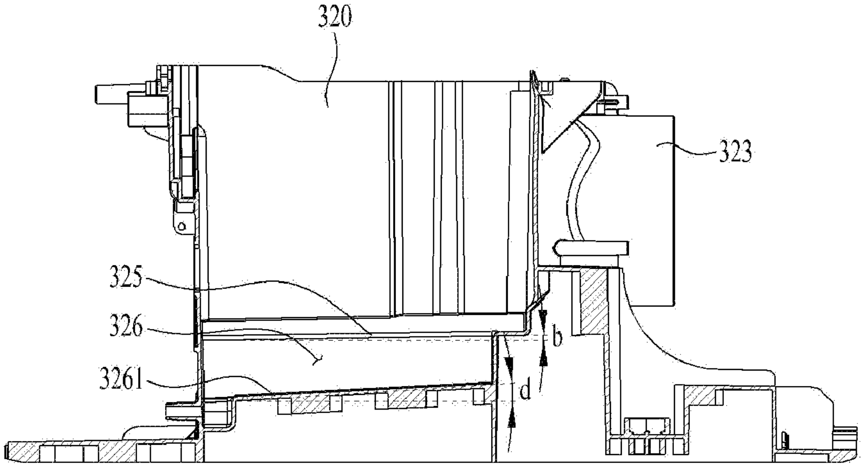

FIG. 11 shows an inclined structure related to the water reservoir.

(a) in FIG. 11 shows a vertical cross-section parallel to the width direction of the base, and (b) in FIG. 11 shows a vertical cross-section parallel to the front and rear direction of the base.

The bottom surface of the circulating duct 320 and a bottom surface of the water reservoir 326 may have a predetermined inclination.

In particular, a bottom surface 325 of the circulating duct may be inclined toward the water reservoir 326, and the bottom surface 3261 of the water reservoir may be inclined toward the drainage pipe 3263.

The bottom surface 325 of the circulating duct may be inclined at an angle 1 'a' toward the water reservoir 326 based on the ground or the bottom surface of the base 310.

Additionally, the bottom surface 325 of the circulating duct may be inclined downward in a forward direction toward the drainage pipe 3263. The bottom surface 325 of the circulating duct may be inclined at an angle 2 'b' in the forward direction based on the bottom surface of the base 310.

As a result, water condensed on the bottom surface of the circulating duct may flow forward and flow toward the water reservoir 326.

In one example, the bottom surface 3261 of the water reservoir may also have a predetermined inclination.

The drainage pipe 3263 may be disposed to be biased to an inner surface of the water reservoir 326 rather than an outer surface thereof.

The bottom surface 3261 of the water reservoir may have a downward inclination toward the inside of the circulating duct 320 based on the bottom surface of the base 310.

The bottom surface 3261 of the water reservoir may be inclined at an angle 3 'c' with respect to the bottom surface of the base 310, and an inclination direction of the bottom surface 3261 of the water reservoir may be opposite to an inclination direction of the bottom surface 325 of the circulating duct.

The angle 3 'c' may be an angle of the downward inclination in a direction away from the partition wall 3211.

The bottom surface 3261 of the water reservoir may be inclined downward toward the drainage pipe 3263.

The bottom surface of the water reservoir 326 may be inclined at an angle 4 'd' to be inclined downward in the forward direction with respect to the base 310.

The above-described angles 1 to 4 may be formed by the molds during the molding process of the base 310. The angles 1 to 4 may be formed during the process of forming the circulating duct 320 or the water reservoir 326. The angle 2 'b' and the angle 4 'd' may form the inclinations in the same direction.

A mold for forming the water reservoir 326 may be withdrawn upward and removed. In this regard, side walls of the water reservoir 326 may be tapered to facilitate the removal of the mold. Specifically, the water reservoir 326 may be formed such that a cross-sectional area thereof increases along on the withdrawal direction of the mold. In other words, a circumference of the top surface of the water reservoir 326 may be greater than a circumference of the bottom surface of the water reservoir 326.

A front surface of the water reservoir 326 may be inclined forward in an upward direction. A rear surface of the water reservoir 326 may be inclined rearward in the upward direction. The left and right side surfaces of the water reservoir 326 may be inclined leftward and rightward in the upward direction, respectively.

Figure 12:
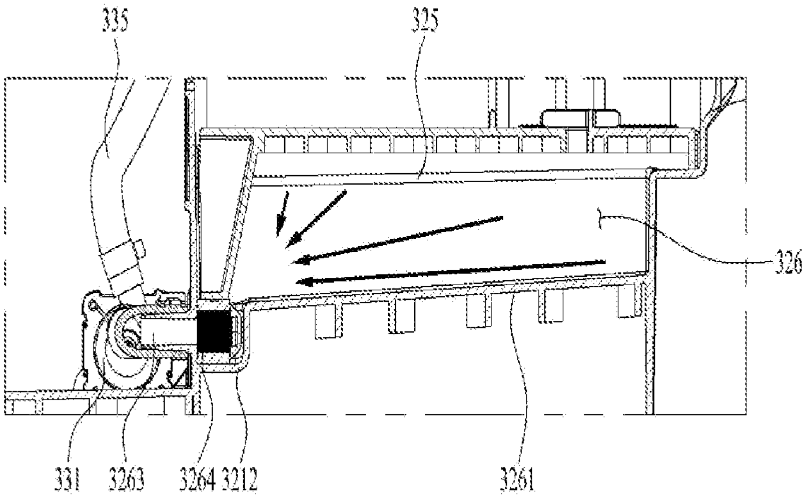
FIG. 12 shows structures of the water reservoir and a residual water treatment unit.
Figure 12:
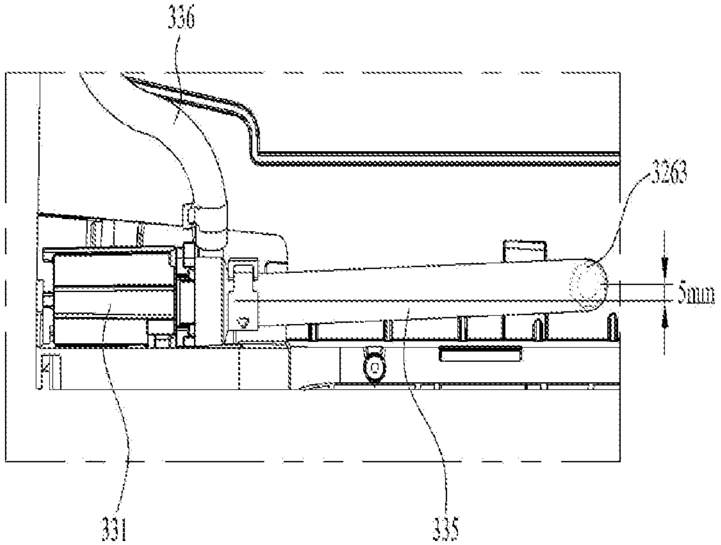

FIG. 12 shows structures of the water reservoir and a residual water treatment unit.

(a) in FIG. 12 shows a cross-sectional view of the water reservoir in the front and rear direction, and (b) in FIG. 12 shows a front side of a bottom surface of the circulating duct 320.

The bottom surface 3261 of the water reservoir 326 may be disposed to be inclined downward in the forward direction, and the bottom surface 325 of the circulating duct 320 may also be disposed to be inclined downward in the forward direction.

A filter 3264 may be disposed in the recessed portion 3262 to prevent foreign substances from being discharged to the outside of the drainage pipe 3263.

The clothing treatment apparatus according to the present disclosure may include a residual water treatment unit 330 that collects water collected in the water reservoir 326 into the water drainage tank 40.

The residual water treatment unit 330 may include a drainage pump 331 that discharges water collected in the water reservoir 326 to the water drainage tank 40. The drainage pipe 3263 and the drainage pump 331 may be connected to each other via a first drainage hose 3351, and water discharged from the drainage pump 331 may flow along a second drainage hose 3352.

The drainage pipe 3263 may be disposed upwardly of the drainage pump 331. Accordingly, water collected in the water reservoir 326 may be collected to the drainage pump 331 by a self-weight thereof.

Figure 13:
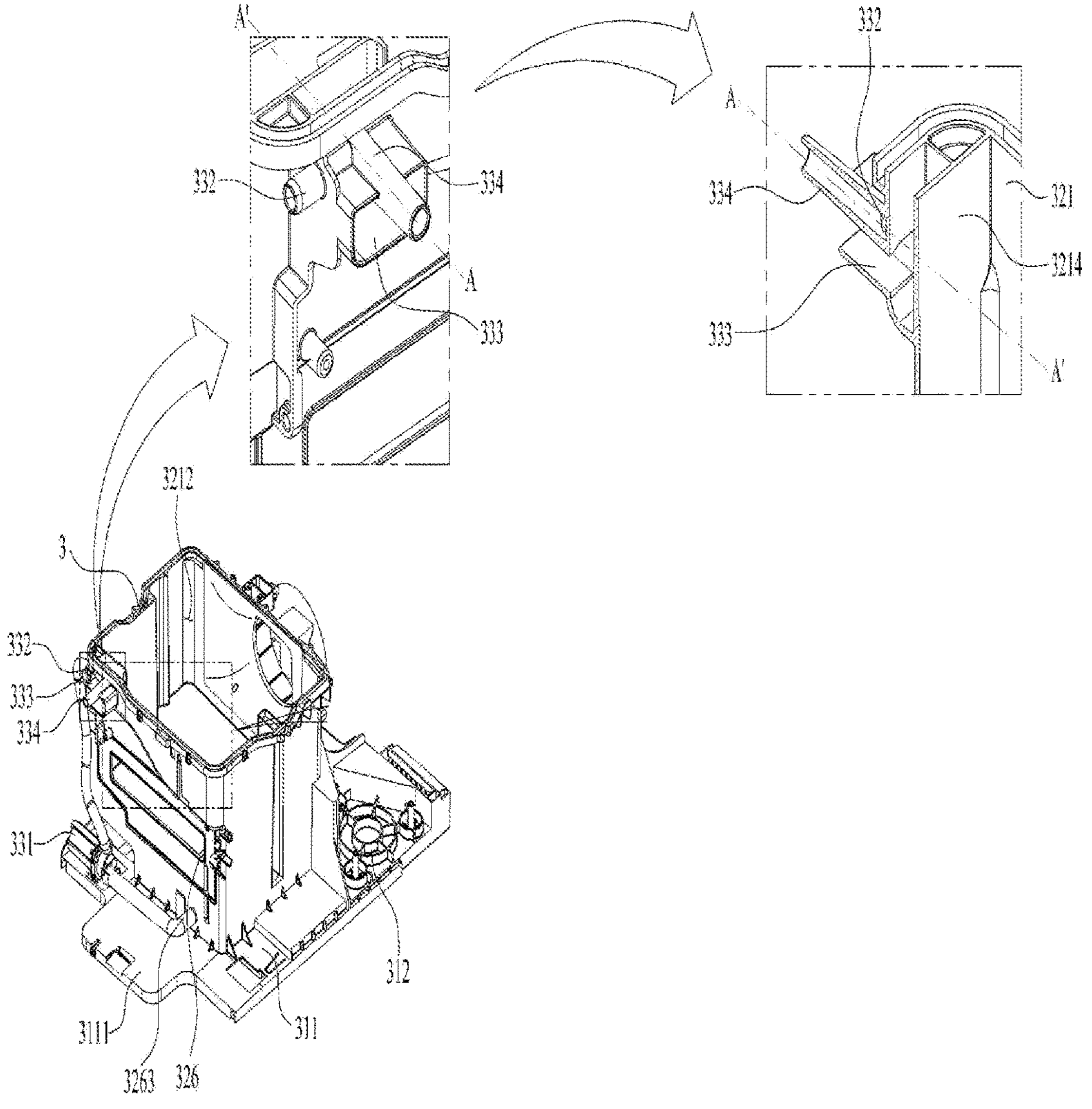
FIG. 13 shows an embodiment of a residual water treatment unit of a clothing treatment apparatus according to the present disclosure.

FIG. 13 shows an embodiment of a residual water treatment unit of a clothing treatment apparatus according to the present disclosure.

Because condensed water collected in the water reservoir 326 should be collected in the water drainage tank 40, the clothing treatment apparatus according to the present disclosure may be equipped with the residual water treatment unit 330 that collects the condensed water in the water drainage tank 40.

In one example, because the water drainage tank 40 is disposed in front of the duct body 321, it may be advantageous for the residual water treatment unit 330 to also be disposed in front of the duct body 321.

In one example, the residual water treatment unit 330 may install some of components connecting the drainage pump 331 with the water drainage tank 40 on the base 310. Accordingly, when the water drainage tank 40 is full or condensed water flows back from the water drainage tank 40, the condensed water may be delivered back into the base 310 and circulated to the water reservoir 326. As a result, condensed water may be prevented from leaking out of the base 310.

The water reservoir 326 may include the drainage pipe 3263 that discharges the condensed water to the outside of the water reservoir 326. The drainage pipe 3263 may extend forward from the base 310.

The residual water treatment unit 330 may include the drainage pump 331 that provides power to deliver water discharged from the drainage pipe 3263 to the water drainage tank 40.

The residual water treatment unit 330 may include an inflow pipe 332 extending from one side of the circulating duct and in communication with the drainage pump 331.

The residual water treatment unit 330 may include a discharge pipe 334 that is in communication with the inflow pipe 332 and delivers the condensed water to the water drainage tank 40, and the discharge pipe 334 may be integrally formed with the base 310.

The residual water treatment unit 330 may further include a guide pipe 333 disposed under the discharge pipe. The guide pipe 333 may be in communication with the water drainage tank 40 and the circulating duct 320. When a water level in the water drainage tank 40 is equal to or higher than a preset water level, the guide pipe 333 may guide water inside the water drainage tank back into the circulating duct 320.

Water guided to the circulating duct 320 may be returned to the water reservoir 326 again and may be guided to the water drainage tank 40 via the residual water treatment unit 330 again.

As a result, even when the water drainage tank 40 is full, the condensed water flows into the circulating duct 320 via the guide pipe 333, so that overflow of water of the water drainage tank 40 may be prevented.

Delete Recovery Flow Channel Configuration Drawing

Figure 14:
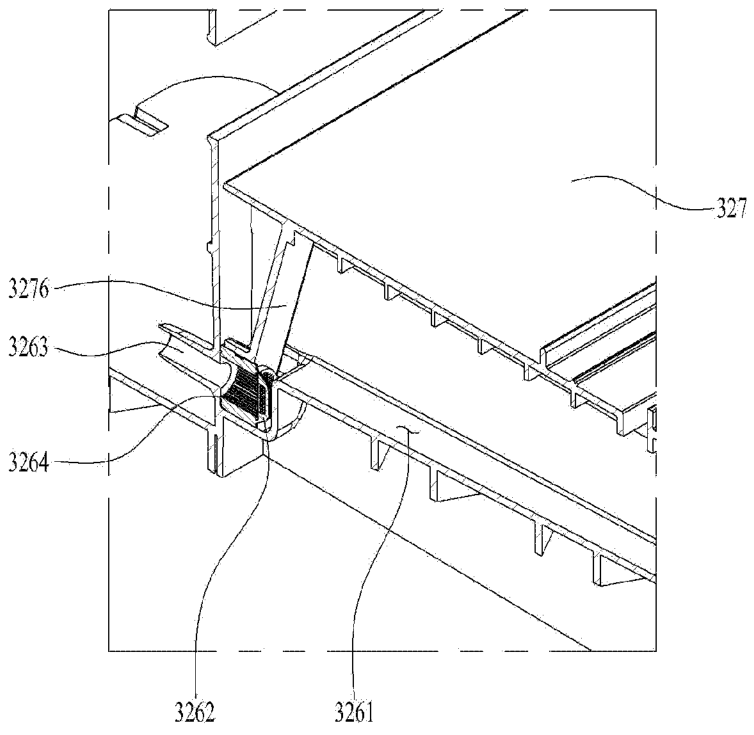
FIG. 14 shows an embodiment of a water cover.

FIG. 14 shows an embodiment of a water cover.

The clothing treatment apparatus according to the present disclosure may further include a water cover 327 seated on the bottom surface of the circulating duct 320. The water cover 327 may support at least one of the evaporator 341 and the condenser 343, and may block water condensed in the evaporator 341 from flowing to the condenser 343 and guide water to the water reservoir 326.

The water cover may prevent the bottom surface of the circulating duct from being exposed to the outside. Additionally, the water cover may form the support surface on which the evaporator and the condenser are supported. The water cover may support the evaporator and the condenser to be spaced apart from the bottom surface of the circulating duct. The water cover may shield the top surface of the water reservoir. In other words, the water cover may perform a function of a cover of the water reservoir.

The water cover 327 may also shield an upper portion of the water reservoir 326. As a result, air introduced into the circulating duct 320 may be prevented from receiving resistance because of a step between the water reservoir 326 and the circulating duct 320.

The water cover 327 may include a water body 3271 that is formed in a plate shape and supports at least one of the evaporator 341 and the condenser 343, and a support rib 3276 that extends downward from the water body 3271 and maintains a vertical level or an inclination of the water body 3271.

One of the support ribs 3276 may be supported on the recessed portion 3262 or the filter 3264. Accordingly, the support rib 3276 may directly guide water flowing along the water body 3271 to the drainage pipe 3263.

Figure 15:
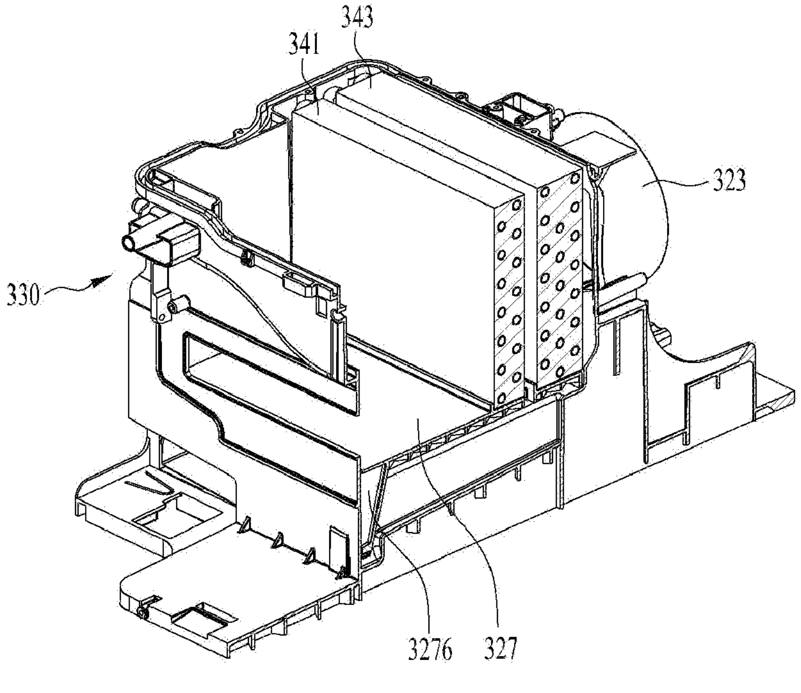
FIG. 15 shows a state in which the water cover is installed on the circulating duct.

FIG. 15 shows a state in which the water cover is installed on the circulating duct.

The water cover 327 may be formed in a shape of a plate that shields at least a portion of the bottom surface of the circulating duct 320.

The water cover 327 may block the water reservoir 326 from being exposed to an area facing the inlet 362 or an area into which outdoor air flows.

The water cover 327 may be disposed to support lower ends of the evaporator 341 and the condenser 343. Even when the bottom surface of the circulating duct 320 is disposed to be inclined because of the water cover 327, the evaporator 341 and the condenser 343 may be disposed at the same vertical level.

Additionally, the water cover 327 may prevent the positions of the evaporator 341 and the condenser 343 from changing.

The water body 3271 of the water cover 327 may be inclined parallel to the base 310. As a result, air introduced into the evaporator 341 may be prevented from receiving unnecessary slope resistance.

Figure 16:
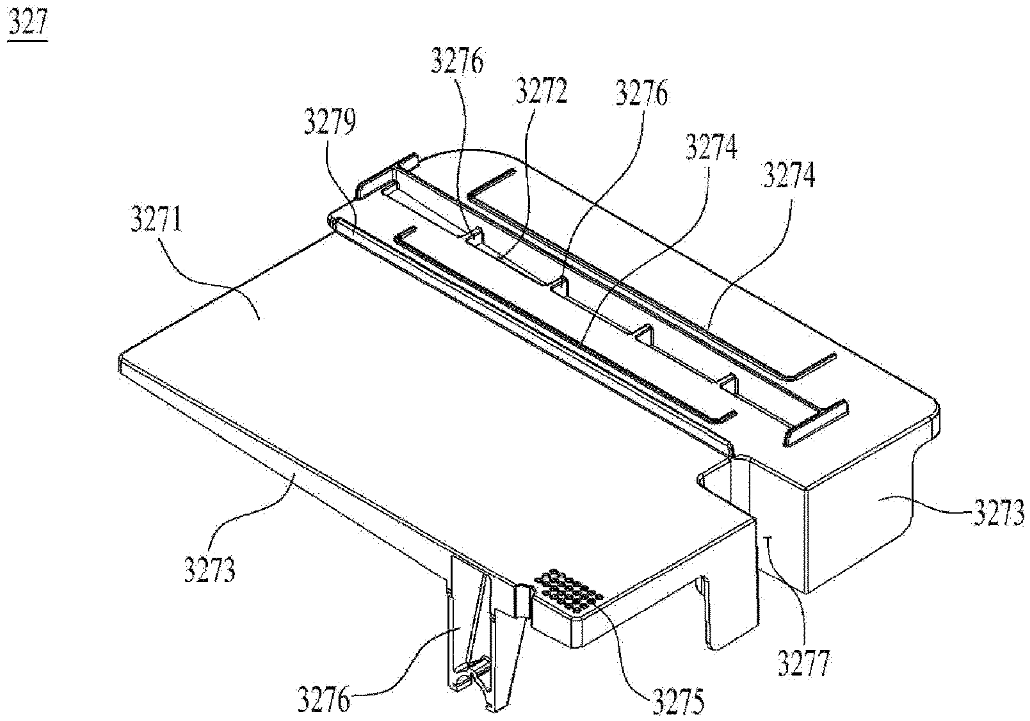
FIG. 16 shows a detailed structure of a water cover.

FIG. 16 shows a detailed structure of a water cover.

The water cover may include the water body 3271 located upwardly of the bottom surface of the circulating duct or the bottom surface of the water reservoir. The water body 3271 may prevent the bottom surface 325 of the circulating duct or the bottom surface 3261 of the water reservoir from being exposed to the outside.

The water cover 327 may include a seating rib 3274 that protrudes upward from the water body 3271. The seating rib 3274 may fix one or more of the evaporator 341 and the condenser 343, and may also maintain a spacing between the evaporator 341 and the condenser 343.

The water cover 327 may include a through-hole 3272 extending through the water body 3271. The through-hole 3272 may be defined between the evaporator 341 and the condenser 343. Accordingly, water condensed in the evaporator 341 may be guided to a space under the water cover.

The water cover 327 may further include a water outlet 3275 that extends through the water body 3271 and is spaced apart from the through-hole 3272. The water outlet 3275 may be defined in an area facing the water reservoir 326.

The water outlet 3275 may discharge water flowing along a top surface of the water body 3271 into the water reservoir 326.

Additionally, the water outlet 3275 may guide water overflowing from the water drainage tank 40 to the water reservoir 326.

The water cover 327 may include a spacing rib 3273 that is disposed on the water body 3271 and is supported on the bottom surface of the circulating duct 320. The spacing rib 3273 may be formed to correspond to the inclination of the bottom surface of the circulating duct 320 and may be in contact with the bottom surface of the circulating duct 320, thereby blocking air from flowing between the water body 3271 and the bottom surface of the circulating duct 320.

In one example, the spacing rib 3273 may be disposed along a perimeter of the water body 3271.

In one example, the water cover 327 may further include an avoidance portion 3277 that prevents interference with the partition wall 3211 of the circulating duct. The avoidance portion 3277 may be formed to be recessed from a side surface of the water body 3271. The avoidance portion 3277 may be formed to correspond to a shape of the partition wall.

The water cover 327 may include a discharge rib 3276 supported on the water reservoir 326. The discharge rib 3276 may be formed in a shape that does not shield the drainage pipe 3263.

Figure 17:
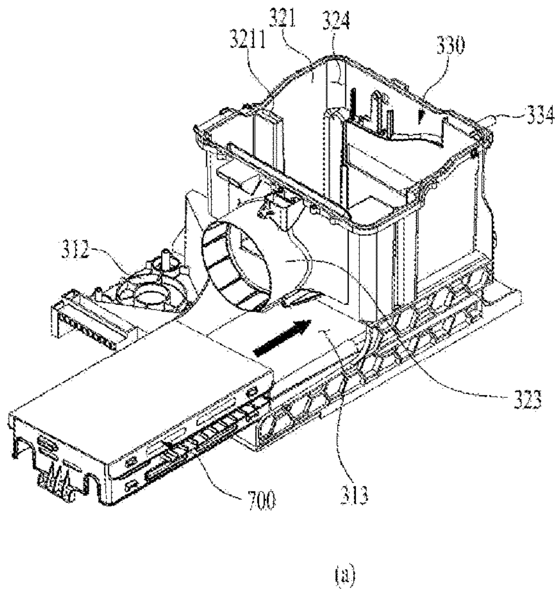
FIG. 17 shows a structure of a controller installation portion disposed on a base of a clothing treatment apparatus according to the present disclosure.
Figure 17:
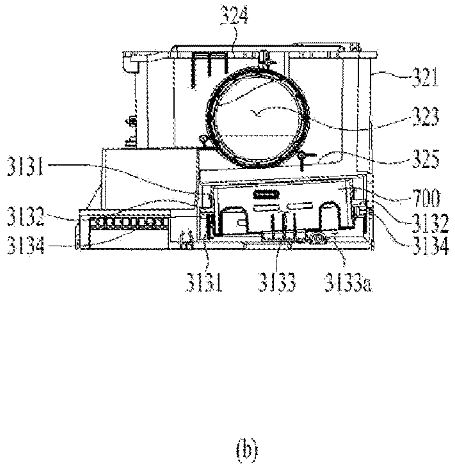

FIG. 17 shows a structure of a controller installation portion disposed on a base of a clothing treatment apparatus according to the present disclosure.

(a) in FIG. 17 shows the controller 700 installed in the controller installation portion 313.

The controller 700 may control all devices necessary for the clothing treatment apparatus according to the present disclosure to perform any course of performing the refreshing stroke on the clothes. The controller 700 may be formed as a PCB board, but may not be limited thereto and may be formed as various devices for control.

The controller 700 may be inserted into and seated in the controller installation portion 313.

The controller installation portion 313 may be defined under the circulating duct 320.

The bottom surface of the circulating duct 320 may form a top surface of the controller installation portion 313. The controller installation portion 313 may be defined downwardly of the air outlet 323.

The controller installation portion 313 may be formed integrally with the base bottom 311. The controller installation portion 313 may be defined as a recessed space under the circulating duct during the process of forming the circulating duct 320 on the base 310.

The controller 700 may be retracted forward into the controller installation portion 313 in a slide manner.

A bracket 3131 that is disposed to surround the controller may be further disposed on a surface of the controller 700. The bracket 3131 may be disposed on top of and beneath the controller to prevent the foreign substances from entering the controller.

Additionally, the bracket 3131 may prevent a circuit board inside the controller 700 from being damaged by heat or vibration being transmitted to the controller 700. The bracket 3131 may be made of metal.

(b) in FIG. 17 shows a state in which a controller is installed in a controller installation portion.

As shown in the drawing above, the controller 700 may be installed at a predetermined angle with the base bottom 311.

For example, the controller 700 may be disposed at an angle toward the water reservoir 326. Accordingly, when water leaks onto a top of the controller 700, the water may quickly leave the controller 700, and the bottom surface of the circulating duct 320 may be formed to be inclined toward the water reservoir 326.

The controller 700 may include a supporter 3132 protruding from a side surface thereof.

The controller installation portion 313 may include ribs 3134 protruding from both side surfaces of the installation portion, respectively. The supporter 3132 of the controller may be mounted on the rib 3134.

The supporter 3132 of the controller may support a load of an entirety of the controller 700. When the supporter 3132 of the controller is supported on the rib 3134, the controller 700 may be spaced a predetermined distance apart from the base bottom 311.

The rib 3134 may be formed integrally with the base 310. The rib 3134 may be molded together when the base 310 is injection molded, and formed integrally with components such as the base bottom 311 and the circulating duct 320.

A protrusion 3133 may be disposed on a front surface of the controller 700. Additionally, a guide protruding rearward may be disposed on an inner surface of the controller installation portion 313. The protrusion may be coupled to the guide. The protrusion may be inserted into the guide. When inserting the controller into the controller installation portion, the controller may be aligned at a correct position by coupling the protrusion to the guide.

Additionally, positions of the both side surfaces of the controller may be determined in a scheme in which the supporter is seated on the rib, as described above. Using such coupling process, the controller may be coupled at the correct position in the controller installation portion without a separate fastening member.

Figure 18:
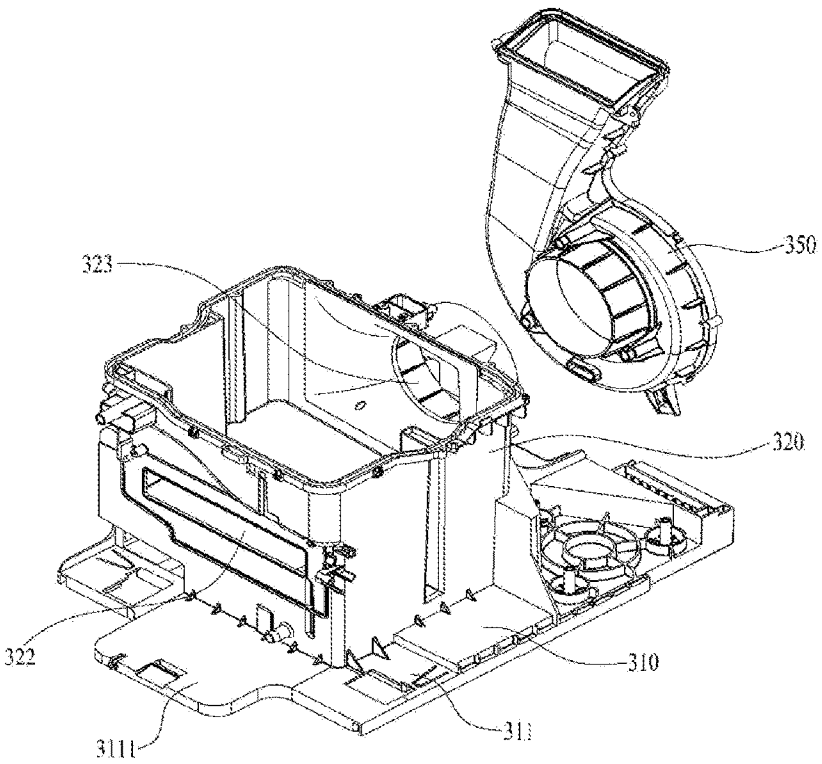
FIG. 18 shows a structure of the air outlet 323 of the clothing treatment apparatus according to the present disclosure.

FIG. 18 shows a structure of the air outlet 323 of the clothing treatment apparatus according to the present disclosure.

The base 310 may include the air outlet 323 that discharges treated air toward the fan housing.

The air outlet 323 may be disposed to allow the inside of the circulating duct 320 or the duct body 321 to be in communication with the fan housing 351. The air outlet 323 may be formed in a bell mouth shape. The air outlet 323 may be formed in the bell mouth shape to reduce the flow loss of air and improve an air circulation efficiency.

The air discharge pipe 3232 of the air outlet 323 may be formed in a shape of a pipe, and during the mold removal process, based on the parting line 3233, the mold disposed in front of the parting line 3233 may be withdrawn forward, and the mold disposed at the rear of the parting line 3233 may be withdrawn rearward.

The fan installation portion 350 may be supported by being coupled to the air discharge pipe 3232. The fan housing 351 may have a coupling hole coupled to an outer circumferential surface of the air discharge pipe 3232, and the blowing fan 353 may be disposed in the coupling hole.

The fan housing 351 may include the discharge duct 352 extending from an outer circumferential surface or an outer side of the blowing fan 353 to the outlet hole 232.

The fan housing 351 and the discharge duct 352 may accommodate the blowing fan 353 therein and form a flow channel through which air may flow.

The motor that rotates the blowing fan 353 may be coupled and supported outside the fan housing 351.

Figure 19:
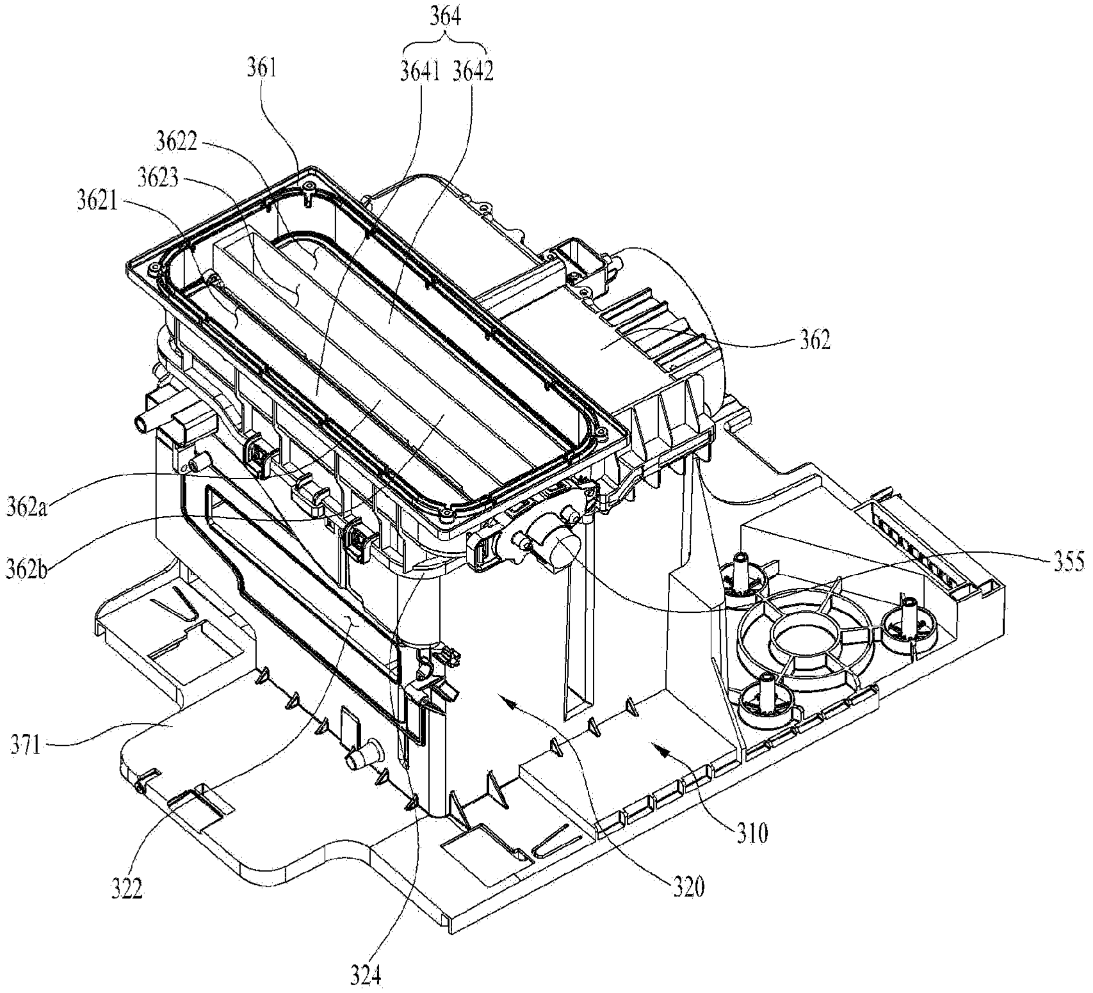
FIG. 19 shows a structure of a base cover of a clothing treatment apparatus according to the present disclosure.

FIG. 19 shows a structure of a base cover of a clothing treatment apparatus according to the present disclosure.

The base cover 360 may be coupled to the top surface of the circulating duct 320 to prevent the inside of the circulating duct 320 from being exposed.

The base cover 360 may include an inflow body 361 that is coupled to the top surface of the circulating duct 320 to allow the inner casing 200 and the circulating duct 320 to be in communication with each other, and a shielding body 363 that extends from the inflow body 361 and shields the circulating duct 320.

The inflow body 361 may be formed in a duct shape to allow the inlet hole 231 of the inner casing and the inside of the circulating duct 320 to be in communication with each other. The inflow body 361 may protrude upwardly of the shielding body 363.

The inflow body 361 may be disposed forwardly of the evaporator 341 so as not to face the evaporator 341 and the condenser 343, and may be disposed forwardly of the partition wall 3211.

The inflow body 361 may serve as an inflow duct that allows air of the inner casing 200 to flow to the circulating duct 320.

The inflow body 361 may include the inlet 362 therein through which air of the inner casing 200 may pass.

Specifically, the base cover 360 may include a first rib **362*a* extending along a width direction of the inflow body 361, and a second rib 362*b* spaced rearwardly apart from the first rib 362*a* and extending along the width direction of the inflow body 361**.

The first rib **362*a* and the second rib 362*b* may be disposed side by side. The first rib 362*a* and the second rib 362*b* may be formed in a plate shape extending in a vertical direction, and may have a vertical dimension corresponding to a vertical dimension of the inflow body 361**.

A front edge of the inflow body 361 and the first rib **362*a* may define a first inlet 3621, the first rib 362*a* and the second rib 362*b* may define a second inlet 3622, and the second rib 362*b* and a rear edge of the inflow body 361 may define a third inlet 3623**.

The first inlet 3621 and the third inlet 3623 may have the same area size, and the second inlet 3622 may have an area size smaller than that of the first inlet 3621 and the third inlet 3623.

The base cover 360 may include a damper 364 that is disposed to open and close the inlet 362, and a driver 365 that is coupled to the damper 364 and controls the opening and closing of the damper 364.

The damper 364 may include a first damper 3641 disposed to open and close the first inlet 3621, and a second damper 3642 disposed to open and close the third inlet 3623.

The first damper 3641 may be formed in a plate shape with an area size corresponding to that of the first inlet 3621, and may be rotatably coupled to both side surfaces of the inflow body 361 inside the first inlet 3621.

The second damper 3642 may be formed in a plate shape with an area size corresponding to that of the third inlet 3623, and may be rotatably coupled to the both side surfaces of the inflow body 361 inside the third inlet 3623.

The second inlet 3622 may be equipped with a blocking filter 366 that allows air to pass therethrough but filters the foreign substances such as fine dust and lint.

The blocking filter 366 may be inserted into the second inlet 3622 to partition the first inlet 3621 and the third inlet 3623 from each other. The blocking filter 366 may extend from the second inlet 3622 to be in contact with the bottom surface of the circulating duct 320.

The blocking filter 366 may be formed as a filter that may filter even the moisture. For example, the blocking filter 366 may be formed as a HEPA filter or the like.

In one example, a shielding member that shields the second inlet 3622 when the blocking filter 366 is inserted into the second inlet 3622 may be further coupled to the second inlet 3622.

The driver 365 may include a motor that provides power to selectively rotate the first damper 3641 and the second damper 3642, and a plurality of gear members that may rotate in engagement with the motor to selectively rotate the first damper 3641 and the second damper 3642.

Because of the driver 365, the first inlet 3621 and the third inlet 3623 may be selectively opened.

Because of the driver 365, air contained inside the inner casing 200 may flow into the circulating duct 320 along the first inlet 3621 or may flow into the circulating duct 320 along the third inlet 3623.

In one example, the driver 365 may control the first damper 3641 and the second damper 3642 to open both the first inlet 3621 and the third inlet 3623, and may control the first damper 3641 and the second damper 3642 to shield both the first inlet 3621 and the third inlet 3623.

The driver 365 may be formed in any structure as long as it may rotate the first damper 3641 and the second damper 3642. For example, the driver 365 may be a combination of the motor, a driving gear rotating by the motor, and a driven gear that is coupled to the first damper and the second damper and rotates by rotation of the driving gear.

The base cover 360 may include the shielding body 363 that may extend from the inflow body 361 and may shield the evaporator 341 and the condenser 343. The shielding body 363 may be formed in a plate shape.

The base cover 360 may be detachably coupled to the top surface of the circulating duct 320 via an inflow hook 3612 extending from a bottom surface of the inflow body 361.

The circulating duct 320 may include a coupling portion that is detachably coupled to the inflow hook 3612.

Figure 20:
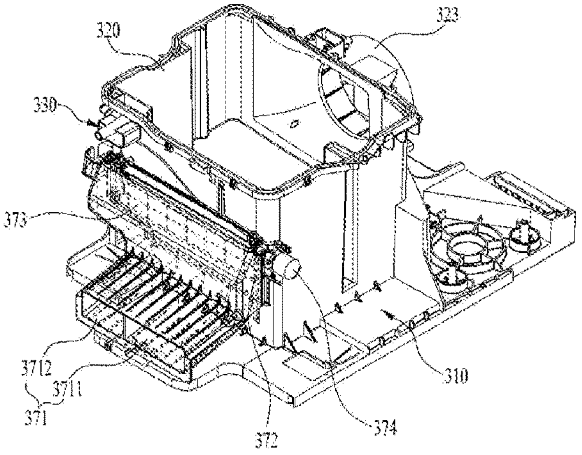
FIG. 20 shows a structure of an outdoor air duct.
Figure 20:
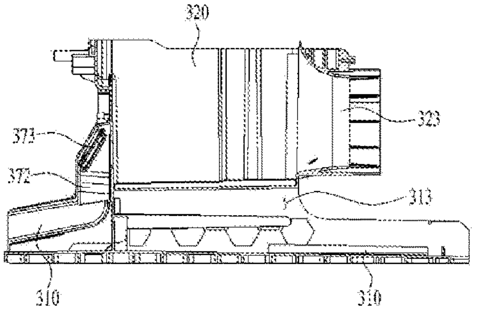

FIG. 20 shows a structure of an outdoor air duct.

Referring to (a) in FIG. 20, the outdoor air duct 370 may be coupled to the base 310.

The outdoor air duct 370 may be in communication with the outdoor air inlet 322.

The outdoor air duct 370 may include an outdoor air damper 373 that opens and closes the outdoor air inlet 322, and an outdoor air driver 374 that rotates the outdoor air damper 373 to selectively open the outdoor air inlet 322.

The outdoor air damper 373 may be formed in a plate shape that may seal the outdoor air inlet 322, and may be rotatably coupled to the both side surfaces of the outdoor air inlet 322.

The outdoor air driver 374 may be formed as an actuator that is coupled to the outdoor air duct 370 or the circulating duct 320 and may be rotates the outdoor air damper 373.

The outdoor air duct 370 may include an extending duct 372 that is located in front of the outdoor air inlet 322 and extends forward from the outdoor air inlet 322, and an intake duct 371 extending forward from the extending duct 372 such that outdoor air may be introduced thereinto.

The intake duct 371 may extend in a space under the extension duct 372, and the water supply tank 30 and the water drainage tank 40 may be disposed thereon. The water supply tank 30 and the water drainage tank 40 may be coupled to or seated on the intake duct 371.

The intake duct 371 may include an outdoor air port 3711 into which outdoor air is sucked at one end or a free end thereof, and a partition rib 3712 that partitions the outdoor air port 3711.

The outdoor air port 3711 may be disposed downwardly of the door 400 so as not to be shielded by the door 400.

The partition rib 3712 may partition the inside of the outdoor air port 3711 and block the foreign substances or a user's body from entering the outdoor air port 3711.

Referring to (b) in FIG. 20, when the outdoor air driver 374 rotates the outdoor air damper 373 to open the outdoor air inlet 322, the intake duct 371 and the circulating duct 320 may be in communication with each other.

In this regard, when the blowing fan 353 operates, air outside the cabinet may flow into the circulating duct 320. When the compressor 342 operates, the outdoor air may be dehumidified while passing through the circulating duct 320 and supplied into the inner casing 200.

The door 400 may further include an exhaust to discharge air inside the inner casing 200 to the outside, and an exhaust damper that selectively opens and closes the exhaust. The exhaust may face the accommodating space of the inner casing 200.

Accordingly, the dehumidified air may be discharged via the exhaust.

Additionally, the outdoor air may be filtered while passing through the blocking filter 366 and discharged back to the outside of the cabinet 100.

Figure 21:
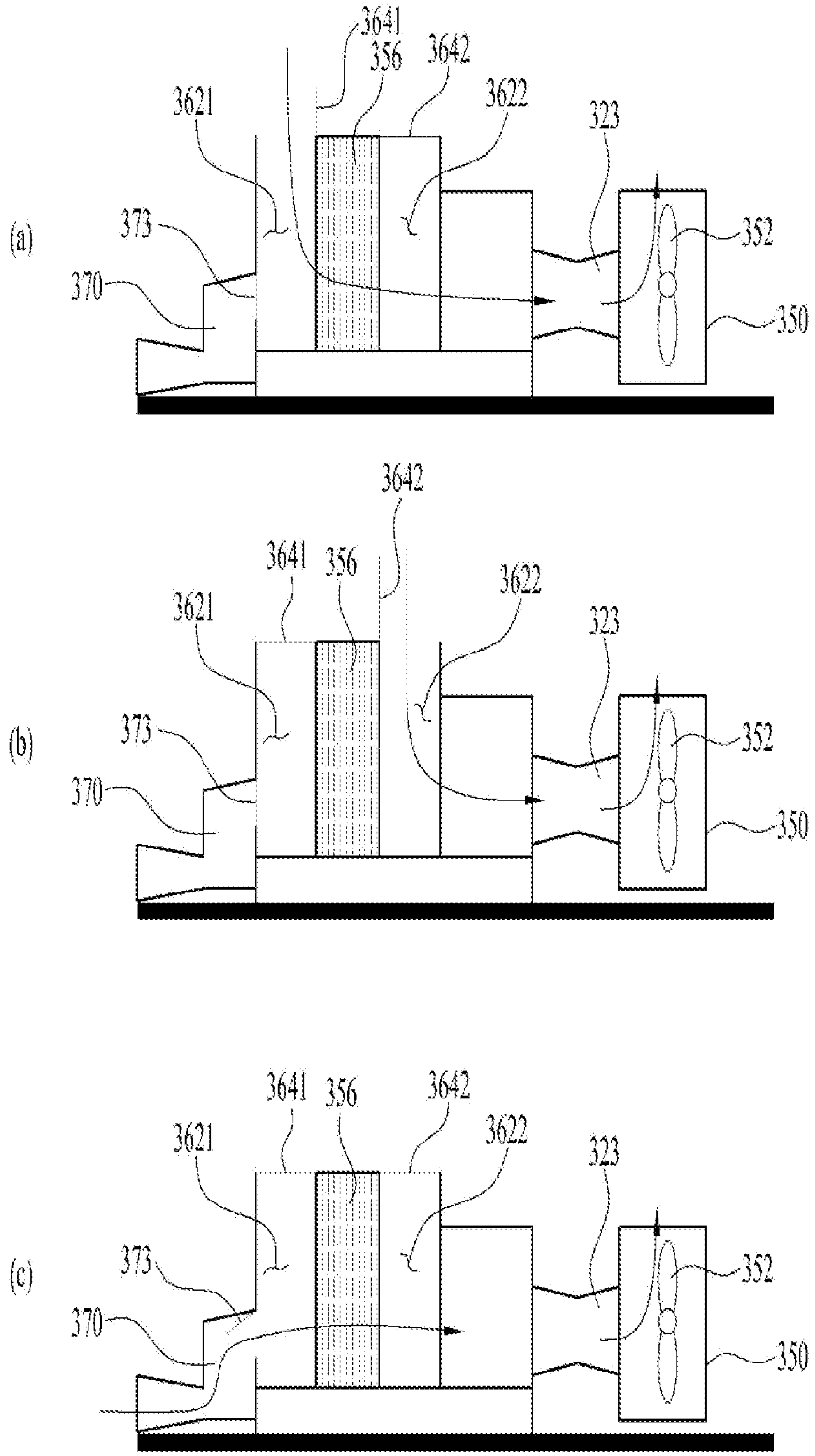
FIG. 21 shows a flow of air flowing through the circulating duct.

FIG. 21 shows a flow of air flowing through the circulating duct.

Referring to (a) in FIG. 21, the outdoor air damper 373 may be controlled to shield the outdoor air inlet 322, the first damper 3641 may be controlled to open the first inlet 3621, and the second damper 3642 may be controlled to shield the third inlet 3623.

When the blowing fan 353 operates, air inside the inner casing 200 may flow into the first inlet 3621 and may be filtered by passing through the filter 366.

When the compressor 342 operates, air that has passed through the filter 366 may be dehumidified and heated while passing through the evaporator 341 and the condenser 343.

Air that has passed through the heat exchanger may pass through the fan installation portion 350 and be supplied into the inner casing 200.

Such state may be a state in which steam has not been supplied to the inner casing 200. This is because when steam is supplied to the inner casing 200, the moisture wets the filter 366 and a performance of the filter 366 is not able to be guaranteed.

As a result, when steam has not been supplied to the inner casing 200, when it is before steam is supplied into the inner casing 200, or when the humidity is lowered even after steam is supplied into the inner casing 200, air inside the inner casing 200 may pass through the first inlet 3621 and pass through the filter 366 to filter the foreign substances such as lint.

Referring to (b) in FIG. 21, the outdoor air damper 373 may be controlled to shield the outdoor air inlet 322, the first damper 3641 may be controlled to shield the first inlet 3621, and the second damper 3642 may be controlled to open the third inlet 3623.

When the blowing fan 353 operates, air inside the inner casing 200 may flow into the third inlet 3623. Because the third inlet 3623 is disposed downstream of the blocking filter 366, air introduced into the third inlet 3623 may not pass through the blocking filter 366.

When the compressor 342 operates, air that has passed through the filter 366 may be dehumidified and heated while passing through the evaporator 341 and the condenser 343.

Air that has passed through the heat exchanger may pass through the fan installation portion 350 and be supplied into the inner casing 200.

As a result, when steam is supplied to the inner casing 200 or when the humidity inside the inner casing 200 is very high, air from the inner casing 200 may be introduced into the third inlet 3623 and may be blocked from entering the first inlet 3621, thereby blocking the blocking filter 366 from being exposed to moisture.

Referring to (c) in FIG. 21, the outdoor air damper 373 may be controlled to open the outdoor air inlet 322, the first damper 3641 may be controlled to shield the first inlet 3621, and the second damper 3642 may be controlled to shield the third inlet 3623.

When the blowing fan 353 operates, air inside the inner casing 200 may be blocked from flowing into the inlet 362, and only outdoor air of the cabinet 100 may flow into the circulating duct 320 and pass through the blocking filter 366. As a result, the foreign substances such as the fine dust contained in outdoor air may be filtered via the blocking filter 366.

When the compressor 342 operates, air that has passed through the filter 366 may be dehumidified while passing through the evaporator 341 and the condenser 343.

Air that has passed through the heat exchanger may pass through the fan installation portion 350 and may be supplied into the inner casing 200 to supply fresh hot air to the clothes.

In this regard, when the door 400 is equipped with a device for discharging air inside the inner casing 200 to the outside, air outside the cabinet may pass through the blocking filter 366 and the heat supply part 340 and may be discharged in the purified and dehumidified state.

As a result, in the clothing treatment apparatus according to the present disclosure, the controller 700 may control the outdoor air driver 374 and the driver 365 to determine flow directions of air inside the inner casing 200 and air outside the cabinet.

Figure 22:
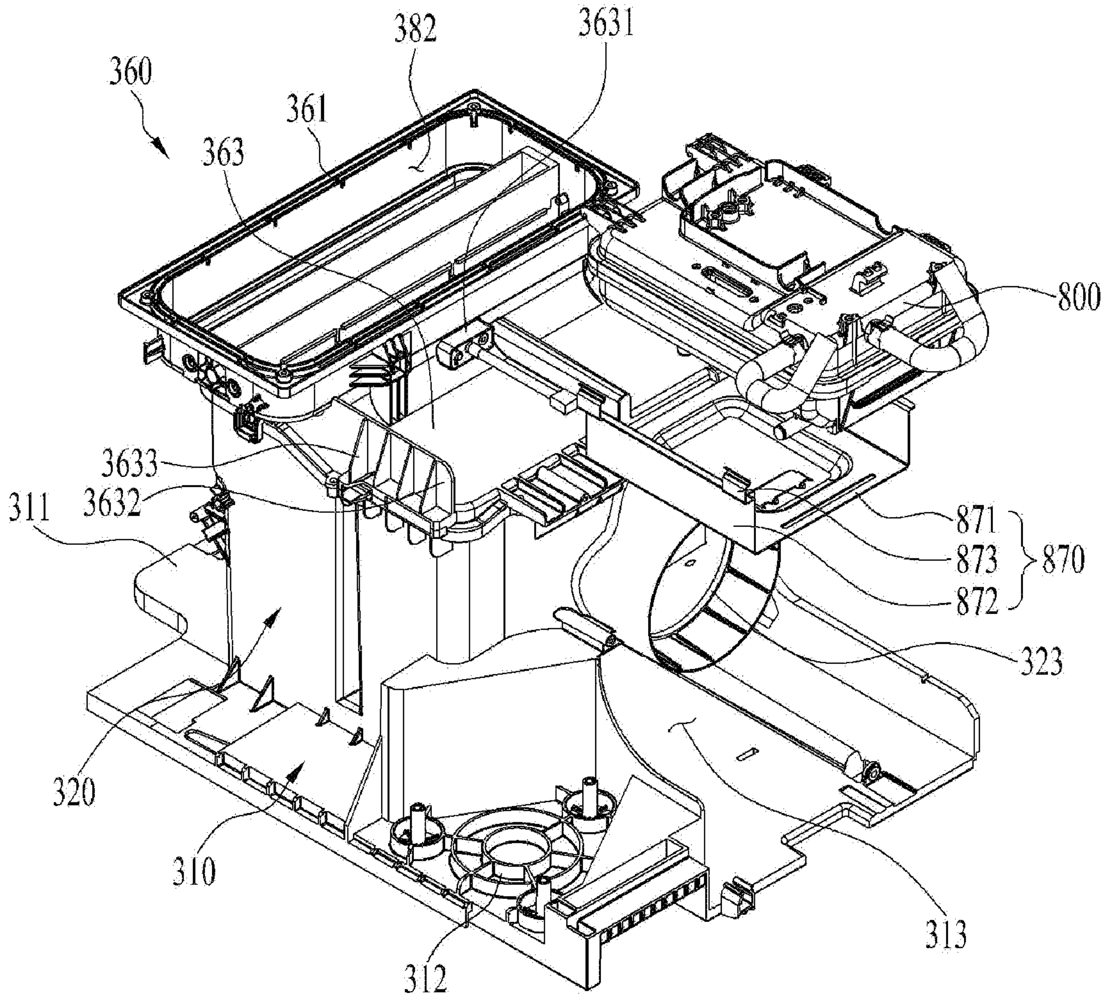
FIG. 22 shows an installation structure of a steam supply.

FIG. 22 shows an installation structure of a steam supply.

The steam supply part 800 may be seated and supported on the base cover 360.

The steam supply part 800 may include a steam casing 810 that is seated on the base cover 360 and stores therein water that generates the steam.

The steam supply part 800 may further include an installation bracket 870 that may fix the steam casing 810 to the base cover 360.

The installation bracket 870 may be coupled to the base cover 360 to fix the steam casing 810.

The installation bracket 870 may include a bottom panel 871 that supports a bottom surface of the steam casing 810 and side panels 872 that support both side surfaces of the steam casing 810 on the bottom panel 871.

The installation bracket 870 may further include one or more fixing clips 873 that extend from the side panel 872 and prevent deviation of the steam casing 810.

The fixing clip 873 may be detachably disposed on top of or on the side surface of the steam casing 810.

The compressor 342 may be disposed downwardly of the steam supply part 800.

The installation bracket 870 may block heat generated from the compressor or heat generated from the refrigerant compressed in the compressor from being transmitted to the steam supply part 800.

The installation bracket 870 may also block fire from spreading to the steam supply part 800 when the fire occurs in the compressor 342.

In one example, the base cover 360 may include a fastener 3631 disposed on the shielding body 363 and detachably coupled to the steam supply part 800. The fastener 3631 may be formed in a structure that is detachably coupled to a protrusion protruding from a lower portion of the steam casing 810.

Accordingly, even when a large amount of water is contained inside the steam casing 810, the steam casing 810 may be stably seated on the base cover 360.

In addition, because the steam casing 810 is disposed upwardly of the circulating duct 320 and thus has a smaller distance from the inner casing 200, condensation of steam generated in the steam casing 810 before reaching the inner casing 200 may be minimized.

Figure 23:
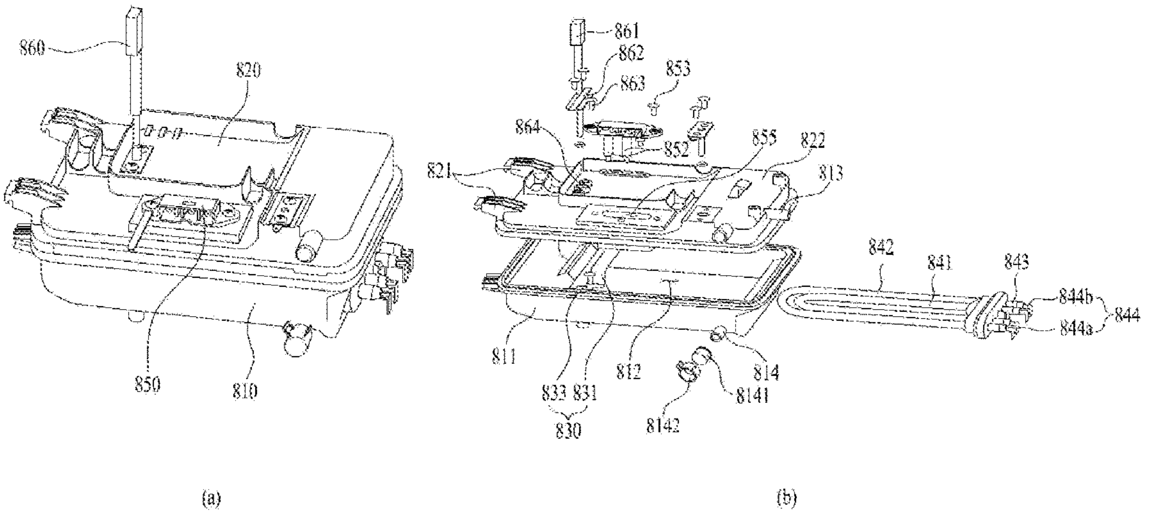
FIG. 23 shows a detailed structure of the steam supply.

FIG. 23 shows a detailed structure of the steam supply.

Referring to (a) in FIG. 23, the steam supply part 800 may include the steam casing 810 that may receive and store water to generate steam, and a heater assembly 840 that is accommodated in the steam casing 810 and heats water to generate steam.

The steam casing 810 may be formed in a shape of a casing with an open top, and may accommodate the heater assembly 840 therein.

The steam supply part 800 may further include a casing cover 820 that is coupled to the steam casing 810 to prevent the heater assembly 840 from being exposed to the outside and to prevent the water from leaking.

The casing cover 820 may be installed with a water level sensor 850 that senses a water level of the steam casing 810, and a steam sensor 860 that senses a temperature inside the steam casing 810 or senses whether steam has been generated inside the steam casing 810.

Referring to (b) in FIG. 23, the steam casing 810 may include a casing body 811 that stores the water therein and provides a space to accommodate the heater assembly 840.

The casing body 811 may have an open top, so that various components may be easily installed inside the casing body 811.

The casing body 811 may include a heater insertion hole 8111 extending through one side thereof and into which the heater assembly 840 may be inserted or through which the heater assembly 840 may be withdrawn.

The casing body 811 may include a recovery pipe 814 that may discharge water contained therein to the outside.

The recovery pipe 814 may be kept closed by a shielding plug 8141 so as to be opened only when residual water inside the steam casing 810 is removed, and may include a shielding clip 8142 that maintains the shielding plug 8141 in a state of being coupled to the recovery pipe 814 to prevent the shielding plug 8141 from being arbitrarily removed.

Accordingly, when repairing the steam casing 810 or preventing freezing and bursting of the steam casing 810, water inside the steam casing 810 may be discharged via the recovery pipe 814.

In one example, a heater fixer 830 that may support or fix the heater assembly 840 may be installed inside the casing body 811. The heater fixer 830 may include a fixing clip 831 that fixes the heater assembly 840, and a clip fastening member 833 that fixes the fixing clip 831 to the casing body 811.

The fixing clip 831 may accommodate therein or surround at least a portion of the heater assembly 840.

In one example, the steam supply part 800 may have a water supply pipe 815 that receives water. The water supply pipe 815 may be in communication with the water supply tank 30 to receive water.

The water supply pipe 815 may be disposed on the casing cover 820 or disposed on the steam casing 810. As a result, water may be prevented from flowing back via the water supply pipe 815.

The steam supply part 800 may include a steam pipe 813 that discharges steam generated by operating the heater assembly 840 to the outside. The steam pipe 813 may also be disposed on the casing cover 820 to block water from being discharged into the steam pipe 813. The steam pipe 813 may be in communication with the steam hole 233 of the inner casing 200.

The casing cover 820 may include a water level sensor hole 854 where the water level sensor may be installed.

The water level sensor 850 may include one or more contact protrusions 852 that are inserted into the water level sensor hole 854 and are immersed in water to sense the water level, and a sensor body 851 that is coupled to the water level sensor hole 854 or supported on the casing cover 820 to maintain the contact protrusions 852 in a floating state inside the steam casing 810.

The sensor body 851 may be coupled to the casing cover 820 via a sensor fastening member 853.

In one example, the casing cover 820 may have an insertion hole 864 into which the steam sensor 860 may be installed. The steam sensor 860 may include a sensing device 861 that is inserted into the insertion hole 864 to sense whether steam is generated inside the steam casing 810, a supporter 863 that fixes the sensing device 861 to the casing cover 820, and a coupling member 862 that couples the supporter 863 to the casing cover 820.

The sensing device 861 may be formed as a humidity sensor or a temperature sensor and sense whether steam is generated inside the steam casing 810.

In one example, the casing cover 820 may include a cover hook 821 that may extend forward and may be coupled to the base cover 360.

In addition, a fixing protrusion 822 that may fix a lower portion of the inner casing 200 or a separate steam discharger 900 may be disposed at a rear side of the casing cover 820.

The heater assembly 840 may be inserted into the heater insertion hole 8111 and accommodated in the steam casing 810, and may receive power to heat water.

The heater assembly 840 may be formed as a sheath heater or the like, and may be controlled by the controller 700 such that operation and stopping may be repeated.

The heater assembly 840 may include a first heater 841 that receives first power and heats water, and a second heater 842 that receives power greater than the first power and heats water.

As a result, the second heater 842 may heat a greater amount of water and generate a greater amount of steam compared to the first heater 841.

The first heater 841 and the second heater 842 may consume portions of a maximum amount of heater power allowed for the heater assembly 840 in a divided manner in the clothing treatment apparatus. That is, when the first heater 841 consumes a portion of the maximum amount of heater power, the second heater 842 may consume the remainder of the maximum amount of heater power.

For example, when a general maximum amount of heater power allowable for the heater assembly 840 is 1500 w, the first heater 841 may consume 600 w and the second heater 842 may consume 880 w. the allocation may be made with 20 w left considering an error or the like.

In one example, the heater assembly 840 may include three or more heaters. For example, the heater assembly 840 may include the first heater 841, the second heater 842, and a third heater 843, and the first heater 841, the second heater 842, and the third heater 843 may consume portions of the maximum amount of heater power in the divided manner.

Hereinafter, a description will be made based on the heater assembly 840 being composed of the first heater 841 and the second heater 842.

The first heater 841 and the second heater 842 may be formed as U-shaped metal pipes.

The heater assembly 840 may include a heater sealer 843 that may fix the first heater 841 and the second heater 842 and seal the heater insertion hole 8111, and may include a terminal 844 that supplies current to the first heater 841 and the second heater 842.

The terminal 844 may include a first terminal **844*a* that supplies the current to the first heater 841 and a second terminal 844*b* that supplies the current to the second heater 842**.

The first heater 841 and the second heater 842 may be disposed at the same vertical level. Accordingly, the first heater 841 and the second heater 842 may generate steam by heating water at the same level.

Accordingly, the controller 700 may adjust an amount of steam generated and an amount of power consumed using both or selectively the first heater 841 and the second heater 842.

Figure 24:
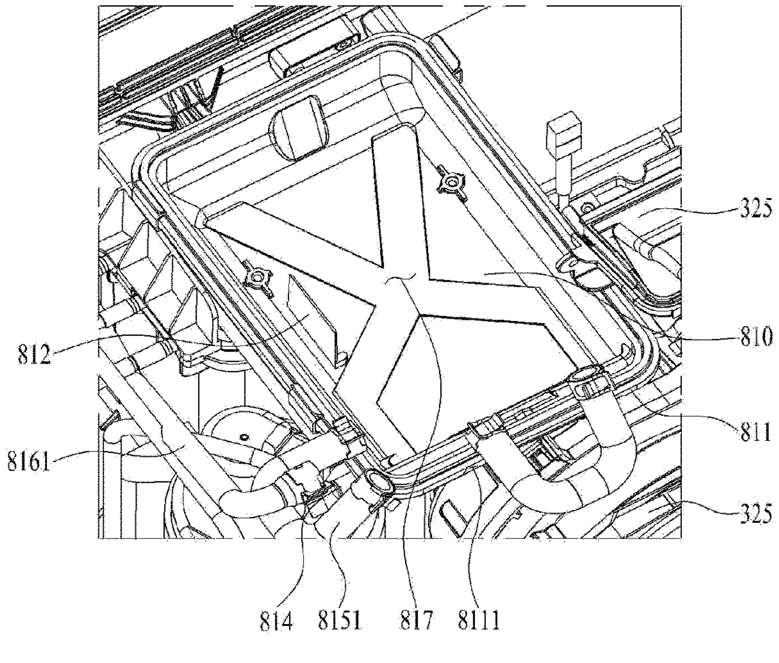
FIG. 24 shows the inside of the steam casing.

FIG. 24 shows the inside of the steam casing.

The steam casing 810 may include a heating space 817 that stores water therein and accommodates the heater assembly 840 therein.

Additionally, the steam casing 810 may receive water to generate steam via a water supply hose 8151 connected to the water supply pipe 815.

In one example, steam generated as the heater assembly 840 operates in the steam casing 810 may be discharged to the outside of the steam supply part 800 along a steam hose 8131 via the steam pipe 813.

The steam hose 8131 may be in communication with the steam hole 233 of the inner casing 200.

In one example, the steam casing 810 may include a separating partition wall 812 that may separate the heating space 817 and the water level sensor 850 from each other. That is, the separating partition wall 812 may separate the heater assembly 840 and the water level sensor 850 from each other, and may be disposed to be biased toward one side of the casing body 811.

The water level sensor 850 may be disposed between the partition wall 812 and an inner surface of the casing body 811.

As a result, vibration of water that occurs when water boils may be prevented from being transmitted to the water level sensor 850, and heat generated in the heater assembly 840 may be prevented from being directly transmitted to the water level sensor 850.

Figure 25:
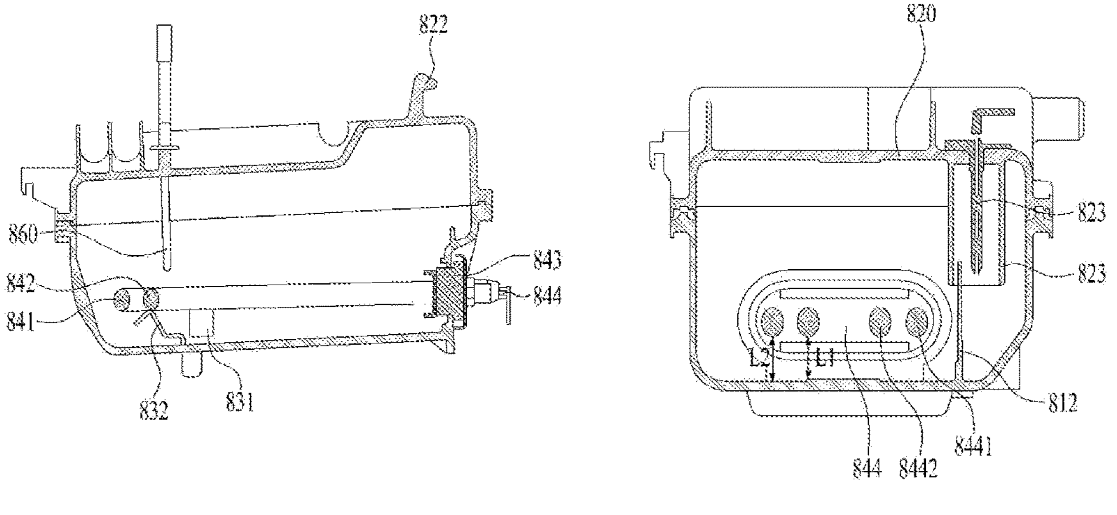
FIG. 25 shows a steam supply in which the heater assembly is installed.

FIG. 25 shows a steam supply in which the heater assembly is installed.

Referring to (a) in FIG. 25, the steam sensor 860 may be disposed upwardly of the heater assembly 840 to sense a temperature inside the steam casing 810 or the like. Accordingly, the steam sensor 860 may sense that steam is generated when the water reaches 100 degrees or a high temperature.

The heater assembly 840 may be supported by a support clip 832 to prevent the heater assembly 840 from being in contact with the bottom surface of the steam casing 810 or the like.

In addition, an upper portion of the heater assembly 840 may be surrounded by the fixing clip 831 to prevent a water level at which the heater assembly 840 is disposed from changing.

Referring to (b) in FIG. 25, the heater sealer 843 of the heater assembly 840 may include a first support hole 8441 through which the first heater 841 extends and is supported and a second support hole 8442 through which the second heater 842 extends and is supported.

A first distance L1 of the first support hole 8441 spaced apart from the bottom surface of the steam casing 810 and a second distance L2 of the second support hole 8442 spaced apart from the bottom surface of the steam casing 810 may be equal to each other.

Even though diameters of the first support hole 8441 and the second support hole 8442 may be different from each other, installation vertical levels thereof may be equal to each other.

Accordingly, the first heater 841 and the second heater 842 may generate steam by heating water at the same level.

Figure 26:
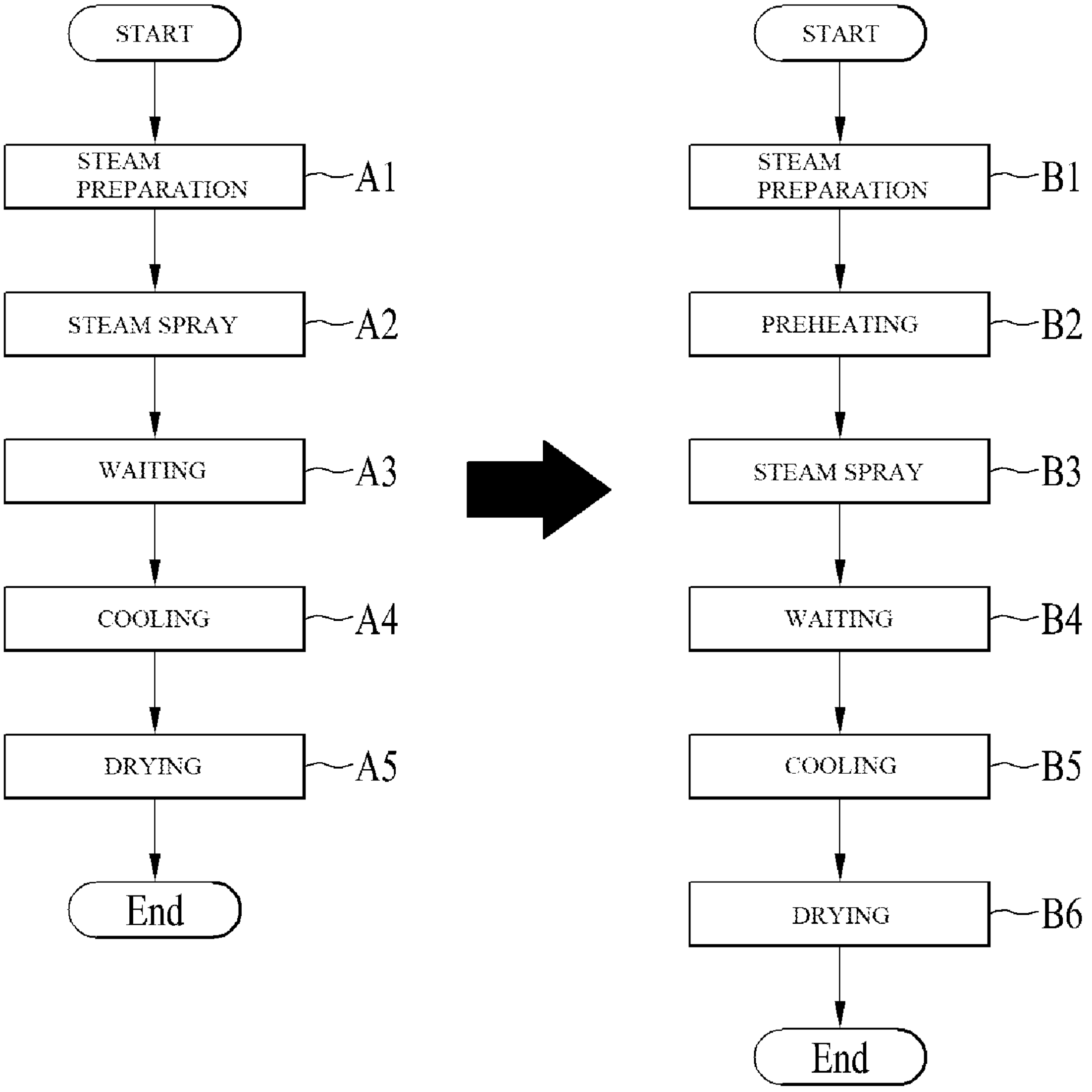
FIG. 26 shows processes in which an existing clothing treatment apparatus and a clothing treatment apparatus according to the present disclosure perform a standard course.

FIG. 26 shows processes in which an existing clothing treatment apparatus and a clothing treatment apparatus according to the present disclosure perform a standard course.

The clothing treatment apparatus according to the present disclosure may have an allowable amount of power set. For example, the allowable amount of power may be smaller than an amount of power consumed when the first heater 841, the second heater 842, and the compressor 342 operate simultaneously.

Additionally, the allowable amount of power may be greater than an amount of power consumed when the first heater 841 and the second heater 842 operate simultaneously.

Additionally, the allowable amount of power may be greater than an amount of power consumed when the first heater 841 and the compressor 342 operate simultaneously.

Additionally, the allowable amount of power may be greater than an amount of power consumed when the second heater 842 and the compressor 342 operate simultaneously.

As a result, the clothing treatment apparatus according to the present disclosure may generate steam by simultaneously operating the first heater 841 and the second heater 842.

In addition, the clothing treatment apparatus according to the present disclosure may simultaneously operate the compressor 342 and one of the first heater 841 and the second heater 842. Accordingly, the steam may be supplied into the inner casing 200, and at the same time, hot air may be supplied into the inner casing 200.

The clothing treatment apparatus according to the present disclosure may simultaneously operate the first heater 841 and the second heater 842 to generate steam quickly at the beginning, but when steam is generated, operate only one of the first heater 841 and the second heater 842 to maintain the generation of steam.

Additionally, the clothing treatment apparatus according to the present disclosure may adjust the steam supply amount by operating only one of the first heater 841 and the second heater 842. Therefore, the refresh stroke may be sufficiently performed even on a material that is vulnerable to moisture and temperature, such as silk or cashmere.

In addition, the clothing treatment apparatus according to the present disclosure may reduce a power consumption required for the steam supply using only one of the first heater 841 and the second heater 842, and may operate the compressor 342 together when supplying steam.

(a) in FIG. 26 shows a method for controlling an existing clothing treatment apparatus.

The existing clothing treatment apparatus performs a steam preparation step A1 of heating water by operating the heater when a course to refresh the clothes is performed, and a steam spray step A2 of supplying the steam to the clothes when water is heated to generate steam.

In this regard, the existing clothing treatment apparatus aims to supply moisture to the clothes in the dry state, so that an amount of steam sprayed is great and the power consumption of the heater is also very great. Therefore, the existing clothing treatment apparatus has a limitation of not being able to simultaneously operate the heater and the compressor.

Therefore, in the steam spray step A2, the existing clothing treatment apparatus operates only the heater.

Thereafter, a waiting step A3 of providing a time period for the clothes to contain moisture with the supplied steam is performed. Thereafter, before operating the compressor, a cooling step A4 of operating only the blowing fan to prevent thermal damage to the clothes is performed. When the temperature inside the inner casing 200 is lowered and the moisture content of the clothes is sufficient, a drying step A5 of operating the compressor is performed.

The refresh stroke such as the deodorization and the wrinkle removal of the clothes may be performed while drying the moisture contained in the clothes via the drying step A5. The drying step A5 has the greatest duration compared to all of the previous operations.

However, the existing clothing treatment apparatus is not able to supply hot air because the compressor is not able to be operated in the steam spray step A2. Therefore, until reaching the drying step A5, the temperature inside the inner casing 200 and a refrigerant temperature of the heat supply part 340 correspond to relatively low temperatures.

Therefore, the existing clothing treatment apparatus is able to guarantee a performance of refreshing, including one of complete drying, sterilization, deodorization, and wrinkle removal of the clothes, only when the drying step A5 continues for a relatively long period of time.

However, the clothing treatment apparatus according to the present disclosure may operate the heater and the compressor simultaneously, as described above. In other words, even when the clothing treatment apparatus according to the present disclosure has a maximum allowable amount of power equal to that of the existing clothing treatment apparatus and has an amount of power used of the entire heaters equal to or similar to that of the existing clothing treatment apparatus, because the plurality of heaters are separated from each other.

Therefore, the clothing treatment apparatus according to the present disclosure may quickly increase the temperature inside the inner casing 200 before the drying step by simultaneously operating the heater and the compressor before the drying step, thereby securing an absolute time period required for the complete drying, the sterilization, the deodorization, and the wrinkle removal of the clothes. As a result, a duration of the drying step may be reduced. In this regard, because the duration of the drying step is set to the greatest, a duration of the entire refresh stroke may be greatly reduced by reducing the duration of the drying step. Additionally, energy efficiency may be greatly increased by reducing an operation duration of the compressor.

(b) in FIG. 26 shows an embodiment of a method for controlling a clothing treatment apparatus according to the present disclosure.

The clothing treatment apparatus according to the present disclosure may perform a steam preparation step B1 of operating the heater assembly 840 to supply steam to the clothes when any course for refreshing or managing the clothes is performed.

The steam preparation step B1 may operate all of the heaters of the heater assembly 840 because the refresh may be reduced as the steam is generated faster.

In other words, in the steam preparation step B1, water may be heated using maximum power of the heater assembly 840.

For example, when the heater assembly 840 is composed of the first heater 841 and the second heater 842, the first heater 841 and the second heater 842 may be operated simultaneously to heat water.

When it is sensed via the sensing device 861 in the steam preparation step B1 that steam is generated inside the steam casing 810, the clothing treatment apparatus according to the present disclosure may perform a preheating step B2 of operating only one of the first heater 841 and the second heater 842.

That is, after steam is generated in the steam casing 810, the steam may be continuously supplied to the inner casing 200 even when only one of the first heater 841 and the second heater 842 is used.

Therefore, in the preheating step B2, afterwards, the temperature inside the inner casing 200 may be increased and the moisture content of the clothes may be increased by supplying steam to the inner casing 200 using only one of the first heater 841 and the second heater 842, and an extra amount of power to be used may be secured.

In the preheating step B2, the clothing treatment apparatus according to the present disclosure may simultaneously operate the compressor 342 to supply hot air to the inner casing 200.

In other words, in the preheating step B2, the compressor 342 and one of the first heater 841 and the second heater 842 may be operated simultaneously. As a result, steam and hot air may be supplied into the inner casing 200 simultaneously. Therefore, the temperature inside the inner casing 200 may be increased from the beginning of the refresh stroke, and a heat exchange performance of the evaporator 341 may be strengthened, thereby also improving a coefficient of performance (cop) of the heat supply part 340.

In addition, because the clothes reach an optimal or minimum temperature required for the refreshing from the preheating step B2, a duration of the subsequent drying step may be greatly reduced.

The preheating step B2 may include a section of simultaneously operating the compressor 342 and one of the first heater 841 and the second heater 842, and a section of operating only the compressor 342.

That is, in the preheating step B2, not only a section in which the heater assembly 840 and the compressor 342 operate simultaneously, but also a section in which only the compressor 342 operates may also exist.

However, it is preferable that the section in which only the compressor 342 operates is placed after the section in which the heater assembly 840 and the compressor 342 operate. When the steam is supplied to the inner casing 200 via the heater assembly 840, not only the temperature inside the inner casing 200 may increase, but also the temperature of the evaporator 341 may increase and moisture may come into contact with the evaporator 341, achieving a great amount of heat exchange with the refrigerant passing through the evaporator 341. Accordingly, a performance of the heat supply part 340 may be improved and the temperature inside the inner casing 200 may be quickly raised.

For example, the preheating step B2 may include a first section of operating the compressor 342 and one of the first heater 841 and the second heater 842, and a second section of stopping the operation of the first heater 841 and the second heater 842 and operating only the compressor 342.

Via the first section, hot air and steam may be supplied to the inner casing 200 to increase the temperature inside the inner casing 200 and an amount of heat in air flowing into the circulating duct 320.

Via the second section, hot air may be supplied in earnest into the inner casing 200 to satisfy a minimum temperature condition for performing the refreshing such as the deodorization, the wrinkle removal, and the sterilization of the clothes.

In the preheating step B2, the second heater 842 may operate more than the first heater 841. As a result, steam may be supplied into the inner casing 200 in an amount greater than that when operating the first heater 841, thereby further increasing the temperature inside the inner casing 200 and the amount of heat in air flowing into the circulating duct 320.

In one example, in the preheating step B2, the first heater 841 may operate and the second heater 842 may not operate. Accordingly, the preheating step B2 may prevent the clothes from being damaged by moisture by spraying a small amount of steam, although the temperature increase of the inner casing 200 is not great. In addition, even when steam is sprayed for a longer period of time, the temperature increase is not great, so that a time period required for the sterilization or the like may be more secured.

The preheating step B2 may be completed when the temperature inside the inner casing 200 reaches a reference temperature, a temperature of air discharged from the inner casing 200 reaches a reference temperature, or a temperature of the refrigerant discharged from the compressor 342 reaches a set temperature. To this end, the clothing treatment apparatus according to the present disclosure may include the temperature sensor disposed inside the inner casing 200 or in the circulating duct 320 to sense the temperature of air or to sense the temperature of the refrigerant discharged from the compressor 342.

In one example, in the preheating step B2, when the temperature inside the inner casing 200 rapidly increases or the temperature of the refrigerant discharged from the compressor 342 exceeds the reference temperature, the operation of the heater assembly 840 may be stopped.

That is, in the preheating step B2, one of the first heater 841 and the second heater 842 may be set to repeat the operation and the stopping (ON/OFF). Because a purpose of the preheating step B2 is to rapidly increase the temperature inside the inner casing 200, time periods during which the first heater 841 and the second heater 842 operate may be set greater than time periods during which the first heater 841 and the second heater 842 are stopped.

When the preheating step B2 is completed, the clothing treatment apparatus according to the present disclosure may perform a steam spray step B3 of supplying steam into the inner casing 200 in earnest. In the steam spray step B3, the first heater 841 and the second heater 842 may operate simultaneously to supply a large amount of steam to the inner casing 200. Therefore, the clothes hung on the inner casing 200 may receive steam in earnest while heated to a certain level in the preheating step B2, thereby increasing the moisture content throughout the clothes.

The steam spray step B3 may be performed for a duration smaller than that of the existing steam spray step A2. This is because a certain amount of steam has already been supplied in the preheating step B2.

When the steam spray step B3 is performed, a drying step B6 of drying the clothes with hot air may be performed immediately. However, a waiting step B4 of waiting for a certain period of time to secure a time period for steam sprayed in the steam spray step B3 to penetrate the entire clothes may be performed.

The waiting step B4 is a state in which the heater assembly 840 and the compressor 342 do not operate. Via the waiting step B4, the clothes may be prevented from being dried before being completely exposed to steam, and thermal damage to the clothes caused by immediate hot air supply in a state in which a surface temperature of the clothes is increased by steam may be prevented.

In one example, the drying step B6 is an operation of operating the compressor 342 to supply hot air to the inner casing 200 in earnest. Therefore, when hot air is supplied immediately in a state in which the temperature inside the inner casing 200 does not fall to a temperature equal to or lower than a safe temperature, the temperature inside the inner casing 200 may rise to a temperature equal to or higher than a limit temperature and the clothes may be damaged.

Therefore, a cooling step B5 of operating the blowing fan 353 may be performed before the drying step B6. In the cooling step B5, the blowing fan 353 may operate and the compressor 342 and the heater assembly 840 may stop operating.

In the cooling step B5, air inside the inner casing 200 may be cooled by circulating along the circulating duct 320.

When the temperature inside the inner casing 200 falls to the temperature equal to or lower than the safe temperature or the cooling step B5 is performed for a required time period, the clothing treatment apparatus according to the present disclosure may perform the drying step B6 of supplying hot air to the clothes.

The drying step B6 may be performed until the moisture content of the clothes falls to a level equal to or lower than the certain level. For example, when there is a lot of moisture in the clothes, when performing the drying step B6, the temperature of air flowing into the circulating duct 320 may be maintained or may not increase rapidly because of vaporization heat.

However, when the clothes are mostly dried, an amount of vaporization heat is small, so that the temperature of air flowing into the circulating duct 320 may rise rapidly. In such scheme, when a dryness of the clothes is secured and a minimum time period required for the refreshing has elapsed, the operation of the compressor 342 may be stopped and the drying step B6 may be ended.

Additionally, in the clothing treatment apparatus according to the present disclosure, the drying step B6 may be ended when a time period during which the clothes are under a temperature equal to or higher than a minimum temperature reaches a minimum time period.

The clothing treatment apparatus according to the present disclosure may further perform the preheating step B2 before the drying step B6 to increase a total time period during which the temperature inside the inner casing 200 is maintained at the temperature equal to or higher than the minimum temperature, thereby greatly reducing the duration of the drying step B6.

In one example, in the clothing treatment apparatus according to the present disclosure, after the compressor 342 operates and then stops in the preheating step B2, the operation of the compressor 342 may be maintained in the stopped state until the drying step B6 is performed.

Figure 27:
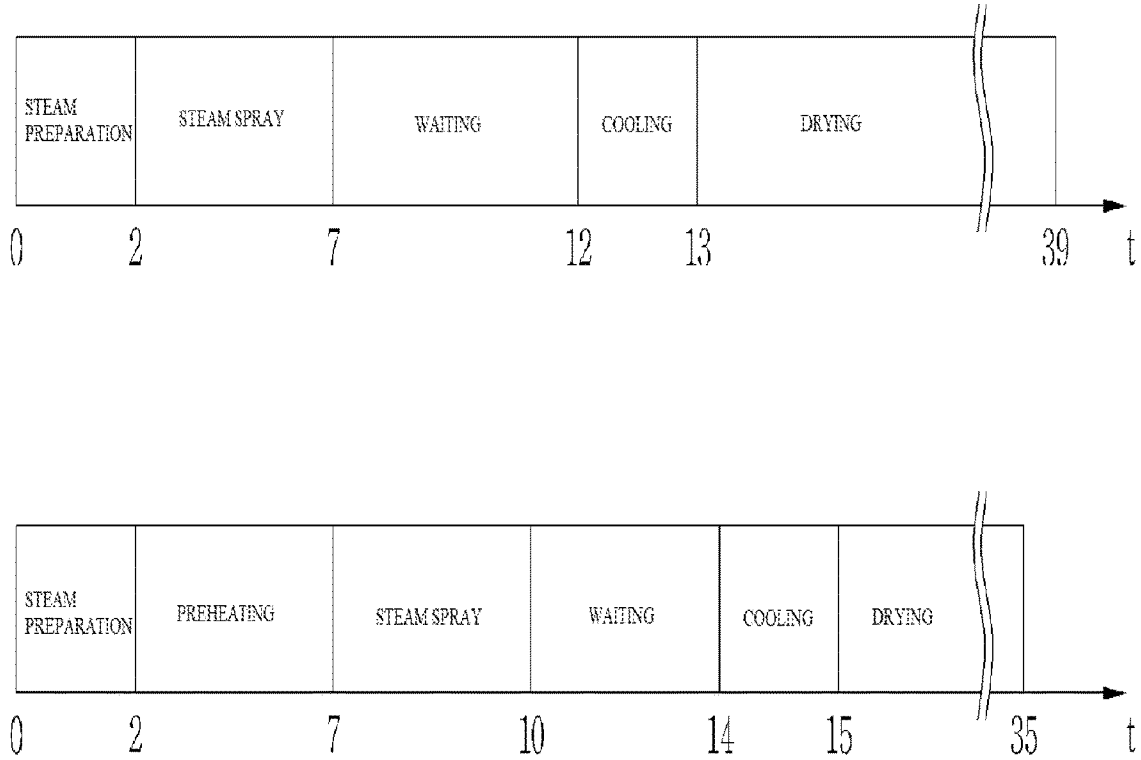
FIG. 27 shows an effect of a clothing treatment apparatus according to the present disclosure.

FIG. 27 shows an effect of a clothing treatment apparatus according to the present disclosure.

(a) in FIG. 27 shows a progression of the most basic standard course performed by an existing clothing treatment apparatus to refresh clothes.

The existing clothing treatment apparatus may perform the steam preparation step A1 of generating steam by heating the heater for about 2 minutes, and may perform the steam spray step A2 of spraying the generated steam into the inner casing 200 for about 5 minutes. Thereafter, the waiting step A3 of not operating the heater assembly 840 and the compressor 342 may be performed for about 5 minutes, and the cooling step A4 of operating the blowing fan 353 may be performed for about 1 minute. Thereafter, the drying step A5 of operating the compressor 342 in earnest to refresh the clothes may be performed for about 26 minutes.

As a result, the existing clothing treatment apparatus may perform the refresh stroke on the clothes for a total of 39 minutes.

Referring to (b) in FIG. 27, the clothing treatment apparatus according to the present disclosure may also perform the steam preparation step B1 of generating steam by operating the heater assembly 840 for about 2 minutes. Because a total rated capacity of the heater assembly 840 of the clothing treatment apparatus according to the present disclosure is not different from the rated capacity assigned to the heater of the existing clothing treatment apparatus, a time period for boiling water to generate steam may be the same.

However, the clothing treatment apparatus according to the present disclosure may perform the preheating step B2 of operating only some heaters of the heater assembly 840 to supply steam into the inner casing 200 for about 5 minutes when steam is generated.

In the preheating step B2, some heaters of the heater assembly 840 and the compressor may operate simultaneously. For example, when the heater assembly 840 includes the two heaters, the first heater 841 and the compressor 342 may operate simultaneously.

When the preheating step B2 is ended, the steam spray step B3 of supplying steam into the inner casing 200 by operating the heater assembly 840 may be performed for 3 minutes. In other words, the steam spray step B3 may be allocated less time period than the steam spray step A2 of the existing clothing treatment apparatus because steam was supplied om the preheating step B2. In the steam spray step A2, all heaters of the heater assembly 840 may operate. As a result, a sufficient amount of steam may be quickly supplied into the inner casing 200. In one example, when necessary, only some heaters of the heater assembly 840 may operate.

In one example, the clothing treatment apparatus according to the present disclosure may perform the steam spray step B3 for the shorter duration, so that the waiting step B4 of not operating the compressor 342 and the heater assembly 840 may also be performed for a shorter duration. For example, the waiting step B4 may be performed for 4 minutes.

The clothing treatment apparatus according to the present disclosure may equally perform the cooling step B5 of operating the blowing fan 353 for 1 minute.

As a result, the clothing treatment apparatus according to the present disclosure further performs the preheating step B2, so that the drying step B6 of operating the compressor 342 may be performed 2 minutes later than the drying step of the existing clothing treatment apparatus.

However, the clothing treatment apparatus according to the present disclosure secures the time period during which the temperature inside the inner casing 200 is maintained at the temperature equal to or higher than the minimum temperature that may promote the refreshing effect via the preheating step B2, so that the duration of the drying step B6 may be significantly reduced.

In addition, in the clothing treatment apparatus according to the present disclosure, the temperature inside the inner casing 200 is maintained higher than that of the existing clothing treatment apparatus because of the preheating step B2, so that the coefficient of performance (COP) of the heat pump is increased, thereby reducing the duration of the drying step B6.

For example, the drying step B6 may only be performed for about 20 minutes.

As a result, the clothing treatment apparatus according to the present disclosure may have an execution duration of the standard course of 35 minutes, thereby further shortening the course execution duration compared to the existing clothing treatment apparatus. Therefore, the energy efficiency is high, and a time period during which the clothes are affected by heat and moisture is reduced, thereby further ensuring durability of the clothes.

Figure 28:
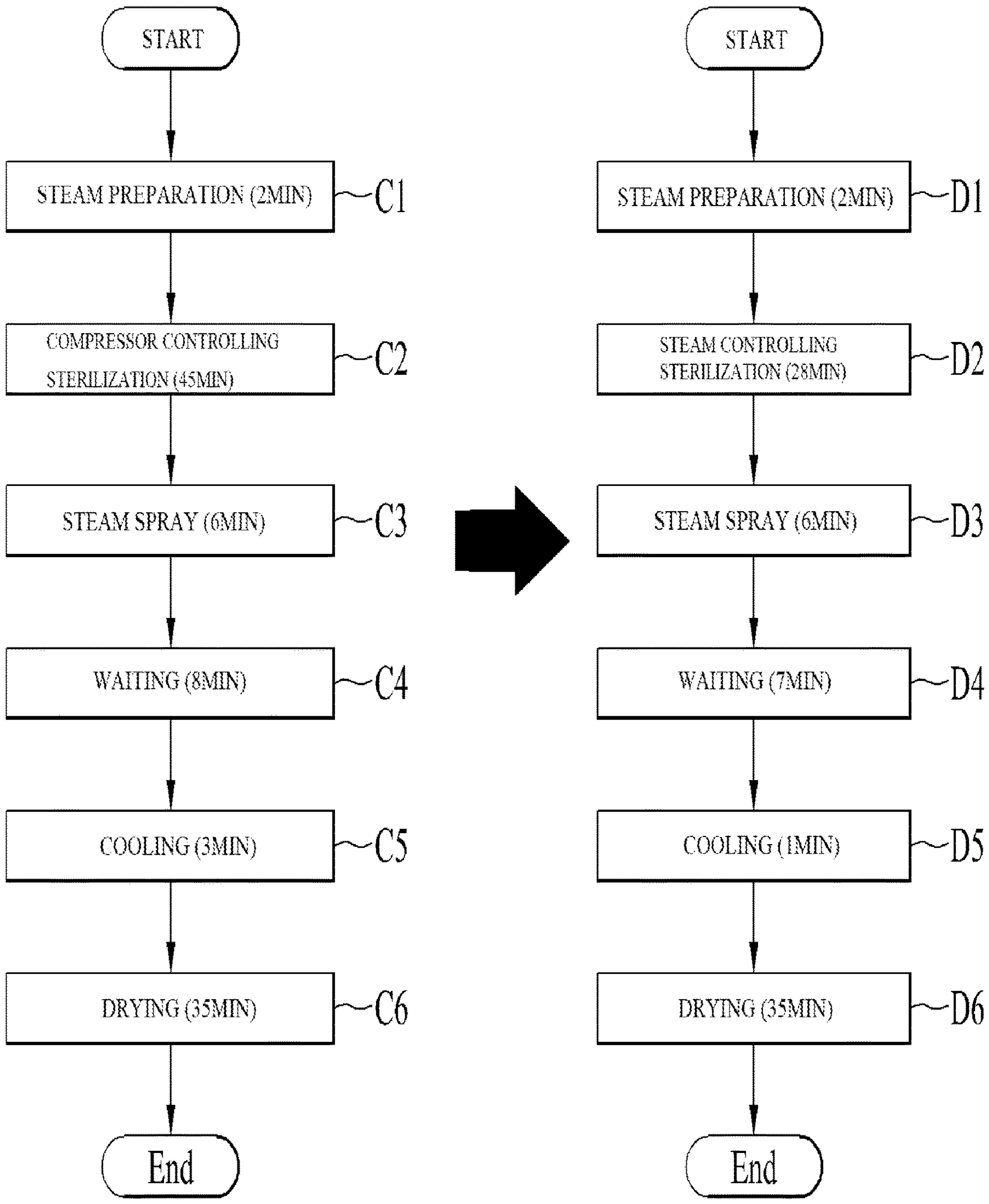
FIG. 28 shows a process in which an existing clothing treatment apparatus and a clothing treatment apparatus according to the present disclosure perform a sterilization course.

FIG. 28 shows a process in which an existing clothing treatment apparatus and a clothing treatment apparatus according to the present disclosure perform a sterilization course.

(a) in FIG. 28 shows the existing clothing treatment apparatus performing the sterilization course.

When the existing clothing treatment apparatus performs the sterilization course, a steam preparation step C1, a steam spray step C3, a waiting step C4, a cooling step C5, and a drying step C6 may be performed in the same manner as the standard course.

Microorganisms, bacteria, and the like may be eradicated only when a sterilization temperature (e.g., equal to or higher than 55 degrees) is maintained for a sterilization time period (e.g., equal to or higher than 25 minutes).

In one example, hot air is supplied in the drying step C6, so that the sterilization may be performed via the same, but a purpose of the drying step C6 is not to maintain the surface temperature of the clothes at a temperature equal to or higher than the sterilization temperature, but to dry the clothes, and the surface temperature of the clothes is not able to be secured to be equal to or higher than the sterilization temperature because of vaporization heat of moisture.

Therefore, the existing clothing treatment apparatus may perform a sterilization step C2 of sterilizing the bacteria before the steam spray step C3.

The existing clothing treatment apparatus operates the compressor in the sterilization step C2 to maintain the temperature inside the inner casing 200 at the temperature equal to or higher than the sterilization temperature for the sterilization time period or longer.

However, at the beginning of the course, the temperature inside the inner casing 200 is low and a sufficient amount of heat is not exchanged in the evaporator, so that the coefficient of performance of the heat pump is low. Additionally, because the inside of the inner casing 200 is dry, the temperature may change rapidly by the supply of hot air.

Therefore, the existing clothing treatment apparatus should operate the compressor longer to reach the sterilization temperature in the sterilization step C2, and, because the temperature inside the inner casing 200 rises rapidly when operating the compressor, should frequently repeat the process of stopping and reoperating the compressor such that the clothes are not thermally damaged.

As a result, the sterilization step of the existing clothing treatment apparatus takes a long period of time, up to 45 minutes.

(b) in FIG. 28 shows a scheme of performing a sterilization course of a clothing treatment apparatus according to the present disclosure.

When the clothing treatment apparatus according to the present disclosure performs the sterilization course, a steam preparation step D1, a steam spray step D3, a waiting step D4, a cooling step D5, and a drying step D6 may be performed in a scheme of operating the compressor, the heater, and the blowing fan, which is the same as that in the standard course.

The clothing treatment apparatus according to the present disclosure may also perform a sterilization step D2 before the steam spray step D3 to maintain the surface temperature of the clothes at the temperature equal to or higher than the sterilization temperature for the sterilization time period.

In the sterilization step D2 of the clothing treatment apparatus according to the present disclosure, the heater assembly 840 and the compressor 342 may operate simultaneously.

Specifically, the clothing treatment apparatus according to the present disclosure may simultaneously operate the compressor 342 and one of the first heater 841 and the second heater 842 in the sterilization step D2.

As a result, the clothing treatment apparatus according to the present disclosure may supply a relatively small amount of steam, thereby preventing the surface of the clothes from being excessively moistened with moisture while increasing the temperature inside the inner casing 200. As a result, when the compressor 342 operates and hot air is supplied, the surface temperature of the clothes may easily rise to the temperature equal to or higher than the sterilization temperature.

Additionally, by increasing specific heat inside the inner casing 200 with the small amount of steam, a temperature increase/decrease rate inside the inner casing 200 may be reduced. Therefore, a temperature increase rate may be low even when an overall average temperature may increase when operating the compressor 342, and a temperature decrease rate may also be low even when the operation of the compressor 342 is stopped.

Therefore, the clothing treatment apparatus according to the present disclosure is very easy to maintain the temperature inside the inner casing 200 at the temperature equal to or higher than the sterilization temperature, thereby greatly reducing a time period during which the operation of the compressor 342 is stopped and the number of times the compressor is stopped and then reoperated.

Moreover, the temperature inside the inner casing 200 may also be precisely controlled via ON/OFF of the heater assembly 840.

Therefore, the clothing treatment apparatus according to the present disclosure may achieve the sterilization time period for which the temperature inside the inner casing 200 is maintained at the temperature equal to or higher than the sterilization temperature in the sterilization step D2 more quickly, thereby significantly reducing a duration of the sterilization step D2.

In one example, in the sterilization step D2, it may be more advantageous to use the first heater 841, which has lower power consumption, than the second heater 842. This is because the temperature inside the inner casing 200 may be increased more gently and it may be easier to maintain the temperature inside the inner casing 200 because an amount of steam supplied to the inner casing 200 is smaller when operating the first heater 841 than when operating the second heater 842.

Additionally, because a small amount of steam is supplied when operating the first heater 841, the moisture content of the surface of the clothes may not be significantly increased.

Therefore, operating the first heater 841 may minimize heat that is lost as evaporation heat even when hot air is supplied to the surface of the clothes compared to operating the second heater 842, so that it may be easier to maintain the surface temperature of the clothes at the temperature equal to or higher than the sterilization temperature.

In addition, in the clothing treatment apparatus according to the present disclosure, it is important to maintain the temperature at the sterilization temperature level during the sterilization time period rather than increasing the temperature inside the inner casing 200, so that it may be more advantageous for sterilization conditions to operate the first heater 841 with a small steam generation amount.

As a result, in the clothing treatment apparatus according to the present disclosure, the heater assembly 840 may operate the heaters in a manner of dividing a maximum heater capacity and may adjust the steam amount, thereby significantly reducing a duration of the sterilization step D2.

For example, the clothing treatment apparatus according to the present disclosure may complete the sterilization step D2 in about 28 minutes. As a result, a duration of the entire sterilization course may be reduced and greater energy savings may be achieved.

Figure 29:
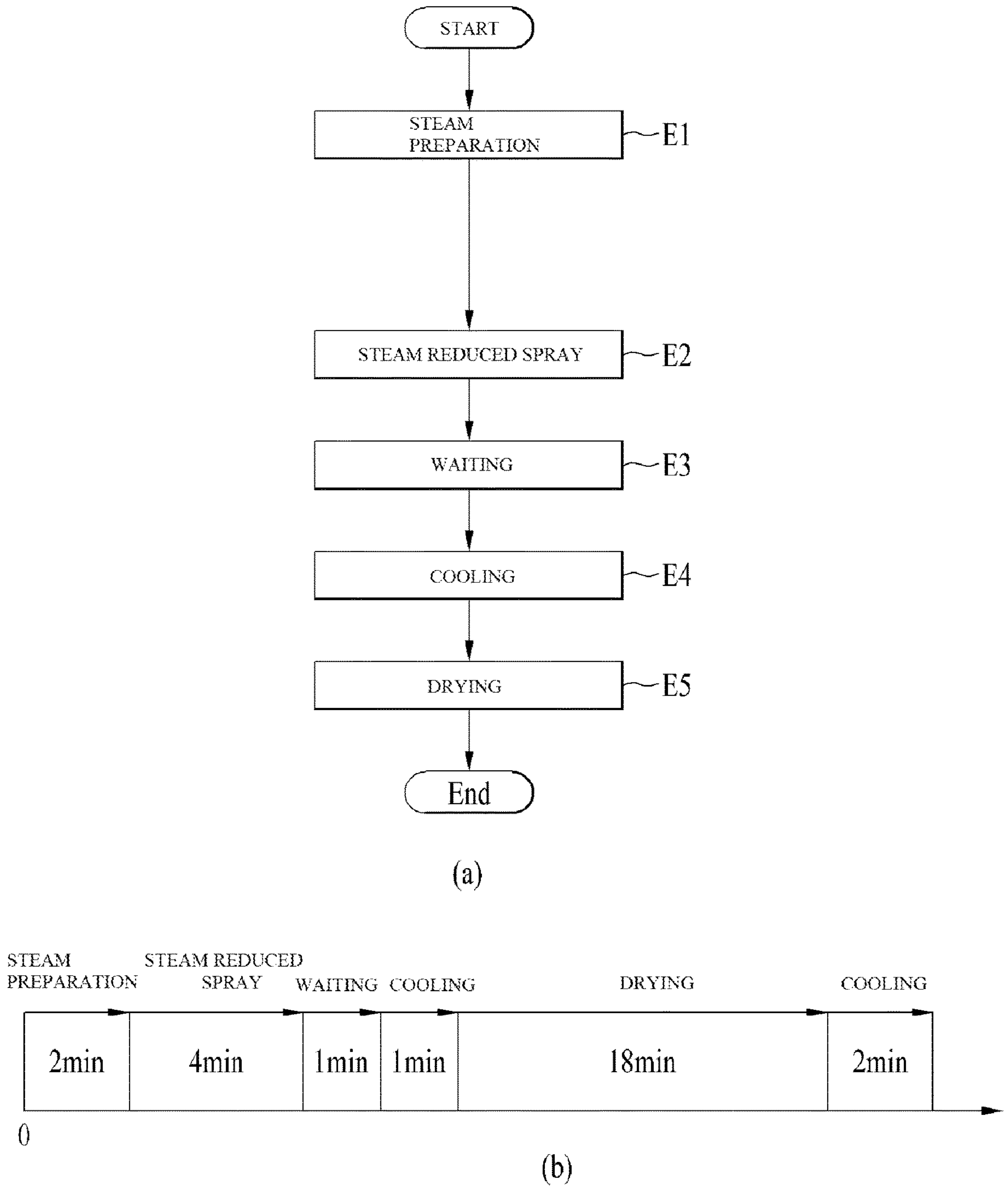
FIG. 29 shows an embodiment in which a clothing treatment apparatus according to the present disclosure treats clothes vulnerable to moisture or temperature.

FIG. 29 shows an embodiment in which a clothing treatment apparatus according to the present disclosure treats clothes vulnerable to moisture or temperature.

Among the clothes, there are vulnerable clothes that may be easily deformed or damaged by moisture and a high temperature.

The existing clothing treatment apparatus should ensure that the dry clothes contains moisture in an amount equal to or greater than a certain amount to refresh the same. Therefore, in the existing clothing treatment apparatus, the rated capacity of the heater is determined such that the heater assembly 840 supplies a large amount of steam. As a result, the existing clothing treatment apparatus has a limitation of not being able to refresh such vulnerable clothes at all.

However, in the clothing treatment apparatus according to the present disclosure, because the heater assembly 840 is equipped with the plurality of heaters that divide the maximum amount of heater power, the amount of steam supplied and the temperature increase rate inside the inner casing 200 when spraying steam may be controlled.

Therefore, the clothing treatment apparatus according to the present disclosure may refresh even such vulnerable clothes.

The clothing treatment apparatus according to the present disclosure may include an inputter that inputs a command or information to the controller 700 on a display panel or the like. The inputter may receive vulnerability information indicating that the clothes accommodated inside the inner casing 200 are vulnerable to moisture or the high temperature.

For example, the inputter may receive the vulnerability information via inputting of a type or a material of the clothes or selecting of the type or the material of the clothes provided by a manufacturer.

As another example, the inputter may receive the vulnerability information via selecting of a course tailored to the vulnerable clothes, such as a cashmere course or a silk course.

When the vulnerability information is input, the clothing treatment apparatus according to the present disclosure may skip the preheating step of simultaneously operating the heater assembly and the compressor after the steam preparation step.

Accordingly, the clothing treatment apparatus according to the present disclosure may prevent the clothes from being damaged caused by the increase in the temperature inside the inner casing 200 or prevent the clothes from being damaged caused by an increase in humidity inside the inner casing 200 by skipping the preheating step.

Additionally, the clothing treatment apparatus according to the present disclosure may operate only one of the first heater 841 and the second heater 842 in the steam spray step after the preheating step. As a result, even in the steam spray step, the amount of steam supplied into the inner casing 200 may be minimized to prevent the clothes from being exposed to moisture.

Thereafter, the waiting step, the cooling step, and the drying step may be performed.

In addition, the clothing treatment apparatus according to the present disclosure may further perform an additional cooling step of additionally operating only the blowing fan 353 after the drying step. Accordingly, by cooling the clothes that are even slightly exposed to the hot air and steam, the clothes may be prevented from being damaged by residual heat or residual humidity before being withdrawn from the inside of the inner casing 200.

For example, the vulnerability information may include cashmere information indicating that the clothes at least partially include a cashmere material.

For example, the cashmere information may correspond to receiving the input of the cashmere course.

When the cashmere course is performed, the clothing treatment apparatus according to the present disclosure may perform a steam preparation step E1 of heating water by operating an entirety of the heater assembly 840.

When the heater assembly 840 is composed of the first heater 841 and the second heater 842, the steam preparation step E1 may be performed to simultaneously operate the first heater 841 and the second heater 842.

When the steam preparation step E1 is completed, the clothing treatment apparatus according to the present disclosure may skip the preheating step and immediately perform a steam spray step E2. In this regard, the steam spray step E2 may be performed as a reduced spray step E2 of operating only one of the first heater 841 and the second heater 842.

Although the cashmere material is vulnerable to moisture, a certain amount of moisture is required for the refreshing, so that the reduced spray step E2 may correspond to operating only the second heater 842.

Therefore, the reduced spray step E2 may have a smaller steam supply amount than the spray step in the standard course or the sterilization course.

Thereafter, when the reduced spray step E2 ends, a waiting step E3 of stopping the operation of the compressor 342 and the heater assembly 840, a cooling step E4 of operating the blowing fan 353, and a drying step E5 of operating the compressor 342 to refresh the clothes may be performed.

In this regard, when the drying step E5 is completed, an additional cooling step E6 of operating the blowing fan 353 may be further performed.

In one example, the reduced spray step E2 in the cashmere course may have a duration smaller than durations of the steam spray steps in the standard course, the sterilization course, and the like.

Additionally, the drying step E5 in the cashmere course may have a duration smaller than durations of the drying steps in the standard course, the sterilization course, and the like.

As such, moisture and heat exposed to the clothes may be minimized, so that even the vulnerable clothes such as the cashmere may be subjected to the refreshing including the deodorization, the wrinkle removal, the foreign substance removal, the drying, and the like.

Figure 30:
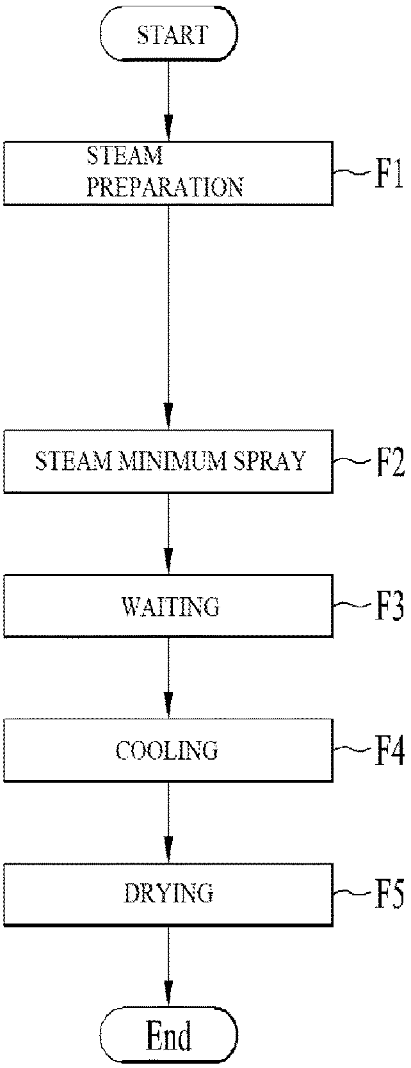
FIG. 30 shows an embodiment in which a clothing treatment apparatus according to the present disclosure treats clothes vulnerable to moisture or temperature.
Figure 30:
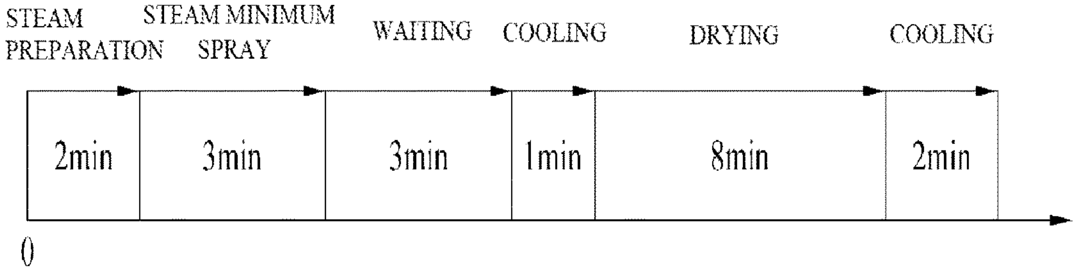

FIG. 30 shows an embodiment in which a clothing treatment apparatus according to the present disclosure treats clothes vulnerable to moisture or temperature.

Among the vulnerable clothes, a material such as silk may be extremely vulnerable to moisture. Therefore, the vulnerable clothes made of the material such as the silk need to be managed more carefully.

The vulnerability information may include silk information indicating that the clothes at least partially include the silk material.

For example, the silk information may correspond to receiving the input of the silk course.

When the silk course is performed, the clothing treatment apparatus according to the present disclosure may perform a steam preparation step F1 of heating water by operating the entirety of the heater assembly 840.

When the heater assembly 840 is composed of the first heater 841 and the second heater 842, the steam preparation step F1 may be performed to simultaneously operate the first heater 841 and the second heater 842.

When the steam preparation step F1 is completed, the clothing treatment apparatus according to the present disclosure may skip the preheating step and immediately perform a steam spray step F2. In this regard, the steam spray step F2 may be performed as a minimum spray step F2 of operating only one of the first heater 841 and the second heater 842.

Because the silk material is very vulnerable to moisture, it is sufficient to maintain minimum humidity to remove the wrinkles. Accordingly, the minimum spray step F2 may correspond to operating only the first heater 841.

Therefore, the minimum spray step F2 may have the smallest steam supply amount compared to those of the spray steps in the standard course, the sterilization course, and the cashmere course.

In one example, in the silk course, the spray step F2 itself may be skipped. In other words, the steam supply itself may not be made into to the inner casing 200.

Thereafter, when the minimum spray step F2 is ended, a waiting step F3 of stopping the operation of the compressor 342 and the heater assembly 840, a cooling step F4 of operating the blowing fan 353, and a drying step F5 of operating the compressor 342 to refresh the clothes may be performed.

In this regard, when the drying step F5 is completed, an additional cooling step F6 of operating the blowing fan 353 may be further performed.

In one example, the minimum spray step F2 in the silk course may have a duration smaller than durations of the steam spray steps in the standard course, the sterilization course, the cashmere course, and the like.

Additionally, the drying step E5 in the silk course may have a duration smaller than durations of the drying steps in the standard course, the sterilization course, and the like.

As such, moisture and heat exposed to the clothes may be minimized, so that even the vulnerable clothes made of the material such as the silk may be subjected to the refreshing including the deodorization, the wrinkle removal, the foreign substance removal, the drying, and the like.

The present disclosure may be modified and implemented in various forms, so that the scope of rights thereof is not limited to the above-described embodiment. Therefore, when the modified embodiment includes components in patent claims of the present disclosure, it should be considered to fall within the scope of the present disclosure.

What is claimed is:

1. A method for controlling a clothing treatment apparatus including a steam supply part including a first heater configured to generate steam to be supplied to an inner casing where clothes are stored, and a second heater disposed separately from the first heater and configured to operate independently of the first heater, and a heat supply part including a heat exchanger configured to heat air to be supplied to the inner casing and a compressor configured to supply a refrigerant to the heat exchanger, the method comprising:

a preparation step of preparing steam to be supplied to the inner casing by operating at least one of the first heater and the second heater;

a spray step of supplying steam to the inner casing by operating at least one of the first heater and the second heater; and a drying step of drying the clothes with air heated by operating the compressor, wherein the first heater and the second heater are configured to generate different amounts of steam from each other, and wherein the method further includes a preheating step of supplying steam to the inner casing by operating only one of the first heater and the second heater, after steam is generated in the preparation step.

2. The method of claim 1, wherein allowable amount of power of the clothing treatment apparatus is set to be smaller than an amount of power required in case that the first heater, the second heater, and the compressor operate simultaneously, and is set to be greater than an amount of power required in case that the compressor and one of the first heater and the second heater operate simultaneously.

3. The method of claim 1, wherein the preheating step includes a section where the compressor and one of the first heater and the second heater simultaneously operate.

4. The method of claim 3, wherein the preheating step includes:

a first section where the compressor and one of the first heater and the second heater simultaneously operate; and a second section where only the compressor operates.

5. The method of claim 3, wherein the second heater is configured to generate more steam than the first heater, wherein the preheating step includes operating the second heater and stopping the operation of the first heater.

6. The method of claim 5, wherein the second heater is controlled to repeat operation and stoppage in the preheating step.

7. The method of claim 6, wherein an operation duration of the second heater is set to be greater than a stopping duration in the preheating step.

8. The method of claim 7, wherein when one of a discharge pressure of the refrigerant from the compressor, a temperature of the refrigerant, and a temperature inside the inner casing is greater than a reference value, the second heater is controlled to stop operating in the preheating step.

9. The method of claim 3, wherein the second heater is configured to generate more steam than the first heater, wherein the preheating step includes operating the first heater and stopping the operation of the second heater.

10. The method of claim 9, wherein an operation duration of the first heater is set to be greater than an OFF duration of the first heater in the preheating step.

11. The method of claim 1, wherein the spray step includes simultaneously operating the first heater and the second heater to supply steam to the inner casing.

12. The method of claim 1, wherein the spray step includes stopping the operation of the compressor.

13. The method of claim 12, further comprising a waiting step of stopping the operation of the compressor, the first heater, and the second heater for a set time period when the spray step ends.

14. The method of claim 13, wherein the clothing treatment apparatus further includes a blowing fan configured to supply air that has passed through the heat exchanger into the inner casing, wherein the method further includes a cooling step of operating the blowing fan but stopping the operation of the compressor when the waiting step ends.

15. The method of claim 1, wherein the drying step includes stopping the operation of the first heater and the second heater.

16. The method of claim 1, wherein the spray step further includes a reduced spray step of operating only one of the first heater and the second heater.

17. The method of claim 1, wherein the clothing treatment apparatus further includes a clothes setter configured to receive vulnerability information indicating that the clothes accommodated in the inner casing are able to be deformed by moisture or high temperature, wherein in case that the vulnerability information is input, the preheating step is skipped.

18. A method for controlling a clothing treatment apparatus including a steam supply part including a first heater configured to generate steam to be supplied to an inner casing where clothes are stored, and a second heater disposed separately from the first heater and configured to operate independently of the first heater, a heat supply part including a heat exchanger configured to heat air to be supplied to the inner casing and a compressor configured to supply a refrigerant to the heat exchanger, and a clothes setter configured to receive vulnerability information indicating that the clothes accommodated in the inner casing are able to be deformed by moisture or high temperature, the method comprising:

a preparation step of preparing steam to be supplied to the inner casing by operating at least one of the first heater and the second heater;

a spray step of supplying steam to the inner casing by operating at least one of the first heater and the second heater; and a drying step of drying the clothes with air heated by operating the compressor, wherein the first heater and the second heater are configured to consume different amounts of power from each other, wherein the method further includes a preheating step of increasing a temperature inside the inner casing by operating the compressor and one of the first heater and the second heater, after steam is generated in the preparation step, and wherein in case that the vulnerability information is input, the preheating step is skipped.

19. The method of claim 18, wherein the spray step includes operating only one of the first heater and the second heater when the vulnerability information is input.

20. The method of claim 19, wherein the clothing treatment apparatus includes a blowing fan configured to supply air that has passed through the heat exchanger into the inner casing, wherein the method further includes an additional cooling step of operating the blowing fan and stopping the operation of the compressor after the drying step when the vulnerability information is input.

21. The method of claim 19, wherein the vulnerability information includes cashmere information indicating that the clothes at least partially include a cashmere material, wherein the spray step includes operating the second heater when the cashmere information is input.

22. The method of claim 18, wherein the second heater is configured to generate more steam than the first heater, wherein the vulnerability information includes silk information indicating that the clothes at least partially include a silk material, wherein the spray step includes operating the first heater when the silk information is input.

23. The method of claim 18, wherein the second heater is configured to generate more steam than the first heater, wherein the vulnerability information includes silk information indicating that the clothes at least partially include a silk material, wherein the spray step is also skipped when the silk information is input.

24. A method for controlling a clothing treatment apparatus including a steam supply part including a first heater configured to generate steam to be supplied to an inner casing where clothes are stored, and a second heater disposed separately from the first heater and configured to operate independently of the first heater, a heat supply part including a heat exchanger configured to heat air to be supplied to the inner casing and a compressor configured to supply a refrigerant to the heat exchanger, and a clothes setter configured to receive a sterilization command to sterilize the clothes accommodated inside the inner casing, the method comprising:

a sensing step of sensing that the sterilization command is input;

a preparation step of preparing steam to be supplied to the inner casing by operating at least one of the first heater and the second heater;

a spray step of supplying steam to the inner casing by operating at least one of the first heater and the second heater; and a drying step of drying the clothes with air heated by operating the compressor, wherein the method further includes a sterilization step comprising operating the compressor and of the first heater and to increase a temperature inside the inner casing to a temperature equal to or higher than a sterilization temperature after steam is generated in the preparation step, and wherein the second heater is configured to generate more steam than the first heater.

25. The method of claim 24, wherein the sterilization step includes a section where the first heater and the compressor simultaneously operate.

26. The method of claim 24, wherein the sterilization step includes controlling the first heater to repeat operating and stopping.

27. The method of claim 26, wherein the sterilization step includes:

stopping the operation of the first heater when the temperature inside the inner casing increase to a temperature equal to or higher than a target temperature; and operating the first heater when the temperature inside the inner casing falls to a temperature equal to or lower than the sterilization temperature.

* * * * *